US005650555A

United States Patent [19]
Somerville et al.

[11] Patent Number: 5,650,555
[45] Date of Patent: Jul. 22, 1997

[54] TRANSGENIC PLANTS PRODUCING POLYHYDROXYALKANOATES

[75] Inventors: Christopher R. Somerville, Okemos; Yves Poirier, East Lansing, both of Mich.; Douglas E. Dennis, Weyers Cave, Va.

[73] Assignee: Board of Trustees Operating Michigan State University, East Lansing, Mich.

[21] Appl. No.: 472,358

[22] Filed: Jun. 7, 1995

Related U.S. Application Data

[63] Continuation of Ser. No. 732,243, Jul. 19, 1991, abandoned.
[51] Int. Cl.$^6$ .............................. A01H 5/00; A01H 1/00; C12N 15/31; C12P 7/62
[52] U.S. Cl. .................. 800/205; 800/250; 435/172.3; 435/135; 435/69.1; 435/320.1; 536/23.7; 47/58
[58] Field of Search ................................ 800/205, 250, 800/255; 435/172.3, 320.1, 69.1, 135; 47/58; 536/23.7

[56] References Cited

U.S. PATENT DOCUMENTS

| | | | |
|---|---|---|---|
| 5,229,279 | 7/1993 | Peoples et al. | 435/135 |
| 5,245,023 | 9/1993 | Peoples et al. | 536/232 |
| 5,250,430 | 10/1993 | Peoples et al. | 435/232 |

FOREIGN PATENT DOCUMENTS

| | | | |
|---|---|---|---|
| 9100917 | of 1991 | WIPO . | |
| 91/00917 | 1/1991 | WIPO | C12P 7/62 |
| 9219747 | of 1992 | WIPO . | |
| 92/19747 | 11/1992 | WIPO | C12N 15/52 |
| 93/02187 | 2/1993 | WIPO | C12N 15/00 |
| 93/02194 | 2/1993 | WIPO | C12N 15/52 |
| 94/11519 | 5/1994 | WIPO | C12N 15/82 |
| 94/23027 | 10/1994 | WIPO | C12N 15/11 |

OTHER PUBLICATIONS

Peoples, O.P. and Sinskey, A. J., Mol. Microbiol 3:349–357 (1989).
Peoples, O.P. and Sinskey, A. J., in Dawes, E.A. (ed) Novel Biodegradable Microbial Polymers, Kluwer Academic Publishers, pp. 191–202, (1990).
Witholt et al., ibid, pp. 161–173 (1990).
Huisman, et al., J. Biol. Chem. 266:2191–2198 (1991).
Steinbuchel, et al., FEMS Microbiol. Rev. Rev. 103:217–230 (1992).
Steinbuchel, A. and Schlegel, H.G., Mol. Microbiol. 5:535–542 (1991).
Doi, Y., in Microbial Polyesters, VCH Publishers pp. 33–98 (1990).
Gerbling, H. and Gerhart, B., Plant Physiol 91:1387–1392 (1989).
Goodwin, T. W. and Mercer, E.L., in Introduction to Plant Biochemistry, Pergamon Press, pp. 162–226 (1983).
Mahler, H.R., in Fatty Acids, their chemistry, properties, production, and uses, [part 3], Markley, K.S. (ed), R.E. Krieger Publishing, pp. 1487–1550 (1983).
Potty, V.H., J. Food Sci. 34:231–234 (1969).
Transgenic Plants, Kung, S.D. and Wu, R. (eds), 297–315 (1993).
Peoples O.P. and Sinskey, A.J., J. Biol. Chem. 264:15298–15303 (1989).
Lloyd, A.M. et al., Science, vol. 234, Oct. 24, 1986 "Transformation of *Arabidopsis thaliana* with *Agrobacterium tumefaciens*" pp. 464–466.
Pool, Robert, Science, vol. 245, Sep. 15, 1989, "In Search of the Plastic Potato" pp. 1187–1189.
Lloyd, A., et al. Science, vol. 234 (1986) pp. 464–466.
Pool, R. Science, vol. 245 (1989) pp. 1187–1189.
Horsch, R., et al. Science, vol. 223 (1984) pp. 496–498.
Anderson, A. and E.A. Dawes, "Occurrence, Metabolism, Metabolic Role, and Industrial Uses of Bacterial Polyhydroxyalkanoates", Microbiol. Rev., vol. 54, No. 4, pp. 450–472 (Dec. 1990).
Archer, E.K. and K. Keegstra, "Current Views on Chloroplast Protein Import and Hypotheses on the Origin of the Transport Mechanism", J. Bioenerg. Biomem., vol. 22, No. 6, pp. 789–810 (no month identified 1990).
Balter, M., "Plastics: A 21st–Century Crop?", International Herald Tribune (Dec. 15, 1989).
Becker, D., "Binary Vectors Which Allow the Exchange of Plant Selectable Markers and Reporter Genes", Nucleic Acids Res., vol. 18, No. 1, p. 203 (Jan. 1990).
Benfey, P.N. and N.H. Chua, "The Cauliflower Mosaic Virus 35S Promoter: Combinatorial Regulation of Transcription in Plants", Science, vol. 250, pp. 959–966 (Nov. 1990).
Bolivar, F., R.L. Rodriguez, P.J. Greene, M.C. Betlach, H.L. Heyneker, H.W. Boyer, J.H. Crosa and S. Falkow, "Construction and Characterization of New Cloning Vehicles", Gene, vol. 2, pp. 95–113 (no month identified 1977).
Boutry, M., F. Nagy, C. Poulsen, K. Aoyagi and N.–H. Chua, "Targeting of Bacterial Chloramphenicol Acetyltransferase to Mitocondria in Transgenic Plants", Nature, vol. 328, pp. 340–342 (Jul. 1987).
Cashmore, A.R., "Nuclear Genes Encoding the Small Subunit of Ribulose–1,5–bisphosphate Carboxylase", in Genetic Engineering of Plants (ed. Kosuge, Meredith and Hollaender), pp. 29–38, Plenum Press NY (no month identified 1983).

(List continued on next page.)

*Primary Examiner*—David T. Fox
*Assistant Examiner*—Charles Rories
*Attorney, Agent, or Firm*—Ian C. McLeod; Brahm J. Corstanje; Jacobus C. Rasser

[57] ABSTRACT

The present invention relates to transgenic plants which produce poly-beta-D-hydroxybutyric acid (PHB) and related polyhydroxyalkanoates (PHA). The production of PHB is accomplished by genetically transforming the plants with modified genes from microorganisms. The genes encode the enzymes required to synthesize PHB from acetyl-CoA or related metabolites. PHB is a very useful polymer which is biodegradable.

38 Claims, 12 Drawing Sheets

OTHER PUBLICATIONS

Chang, S.S., S. -K. Perk, and H.-G. Nam, "Transformation of Arabidopsis by Agrobacterium Inoculation on Wounds", Abstract in: Fourth International Conference on Arabidopsis Research, Vienna (no month identified 1990).

Cheung, A.Y., L. Bogorad, M. Van Montagu and J. Schell, "Relocating a Gene for Herbicide Tolerance: A Chloroplast Gene is Converted into a Nuclear Gene", Proc. Natl. Acad. Sci., vol. 85, pp. 391–395 (Jan. 1988).

Dawes, E.A. and P.J. Senior, "The Role and Regulation of Energy Reserve Polymers in Microorganisms", Adv. Microb. Physiol., vol. 10, pp. 135–266 (no month identified 1973).

Doi, Y., "Introduction", in Microbial Polyesters, VCH Publishers, Chapter 1, pp. 1–9 (no month identified 1990).

Doi, Y., "Microorganisms and Poly(3–hydroxyalkanoates)", in Microbial Polyesters, VCH Publishers, Chapters 3, 4, & 5, pp. 33–98 (no month identified 1990).

Doi, Y., "Structure and Properties of Poly(3–hydroxybutyrate)", in Microbial Polyesters, VCH Publishers, Chapter 6, pp. 99–105 (no month identified 1990).

Downey, R.K. and G. Röbbelen, "Brassica Species", In: Oil Crops of the World, Robbelen, Downey and Ashri (eds), Chapter 16, pp. 339–363, McGraw–Hill, New York (no month identified 1989).

Estelle, M.A. and C. Somerville, "Auxin–resistant Mutants of *Arabidopsis thaliana* with an Altered Morphology", Mol. Gen. Genet., vol. 206, No. 2, pp. 200–206 (no month identified 1987).

Feinberg, A.P. and B. Volgelstein, "A Technique for Radiolabeling DNA Restriction Endonuclease Fragments to High Specific Activity", Anal. Biochem., vol. 132, pp. 6–13 (Jul. 1983).

Friedmann, A.L. and K. Keegstra, "Chloroplast Protein Import, Quantitative Analysis of Precursor Binding", Plant Physiol., vol. 89, pp. 993–999 (no month identified 1989).

Fukui, T., A. Yoshimoto, M. Matsumoto, S. Hosokawa, T. Saito, H. Nishikawa and K. Tomita, "Enzymatic Synthesis of Poly–βHydroxybutyrate in *Zoogloea ramigera*", Arch. Microbiol., vol. 110, pp. 149–156 (no month identified 1976).

Gatenby, A.A., T.H. Lubben, P. Ahlquist and K. Keegstra, "Imported Large Subunits of Ribulose Bisphosphate Carboxylase/Oxygenase, But Not Imported β–ATP Synthase Subunits, Are Assembled into Holoenzyme in Isolated Chloroplasts", EMBO J., vol. 7, No. 5, pp. 1307–1314 (no month identified 1988).

Gerbling, H. and B. Gerhart, "Peroxisomal Degradation of Branched–chain 2–Oxo Acids[1,2]", Plant Physiol., vol. 91, pp. 1387–1392 (Jul. 1989).

Goodwin, T.W. and E.L. Mercer, "Respiration", In Introduction to Plant Biochemistry, Pergamon Press, Chapter 6, pp. 162–226 (no month identified 1983).

Gross, R.A., C. De Mello, R.W. Lenz, H. Brandl and R.C. Fuller, "Biosynthesis and Characterization of Poly(β–hydroxyalkanoate Produced by *Pseudomonas oleovorans*", Macromolecules, vol. 22, No. 3, pp. 1106–1115 (no month identified 1989).

Hanahan, D., "Studies on Transformation of *Escherichia coli* with Plasmids", J. Mol. Biol., vol. 166, pp. 557–580 (Jan. 1983).

Harwood, J.L., "Fatty Acid Metabolism", Ann. Rev. Plant Physiol. Plant Mol. Biol., vol. 39, pp. 101–138 (no month identified 1988).

Haughn, G.W., J. Smith, B. Mazur and C.R. Somerville, "Transformation With a Mutant Arabidopsis Acetolactate Synthase Gene Renders Tobacco Resistant to Sulfonylurea Herbicides", Mol. Gen. Genet., vol. 211, pp. 266–271 (no month identified 1988).

Haywood, G.W., et al., "The Importance of PHB–synthase Substrate Specificity in Polyhydroxyalkanoate Synthesis by *Alcaligenes eutrophus*", FEMS Microbiol. Lett., vol. 57, pp. 1–6 (no month identified 1989).

Hiatt, A., R. Cafferkey and K. Bowdish, "Production of Antibodies in Transgenic Plants", Nature, vol. 342, pp. 76–78 (Nov. 1989).

Holmes, P.A., "Applications of PHA—A Microbially Produced Biodegradable Thermoplastic", Phys. Technol., vol. 16, No. 1, pp. 32–36 (no month identified 1985).

Holmes, P.A., "Biologically Produced (R)–3–hydroxyalkanoate Polymers and Copolymers", In Developments in Crystalline Polmers–2, Basset, D.C. (ed), pp. 1–65 (no month identified 1988).

Horsch, R., R.T. Fraley, S.G. Rogers, P.R. Sanders, A. Lloyd and N. Hoffmann, "Inheritance of Functional Foreign Genes in Plants", Science, vol. 223, pp. 496–498 (Feb. 1984).

Huisman, G.W., E. Wonink, R. Meima, B. Kazemier, P. Terpstra and B. Witho, "Metabolism of Poly(3–hydroxyalkanoates)(PHAs) by *Pseudomonas oleovorans*", J. Biol. Chem., vol. 266, No. 4, pp. 2191–2198 (Feb. 1991).

Huisman, G.W., O. de Leeuw, G. Eggink and B. Witholt., "Synthesis of Poly–3–hydroxyalkanoates Is a Common Feature of Fluoresent Pseudomonads", Applied and Environmental Microbiology, vol. 55, No. 8, pp. 1949–1954 (Aug. 1989).

Janes, B.B., J. Hollar and D. Dennis, "Molecular Characterization of the Poly–β–Hydroxybutyrate Biosynthetic Pathway of *Alcaligenes eutrophus* H16", in Novel Biodegradable Microbial Polymers, Dawes, E.A. (ED.), Kluwer Academic Publishers, pp. 175–190 (no month identified 1990).

Jorgensen, R., "Altered Gene Expression in Plants Due to Trans Interactions Between Homologous Genes", Trends in Biotechnology, vol. 8, pp. 340–344 (Dec. 1990).

Keegstra, K. and L.J. Olsen, "Chloroplastic Precursors and Their Transport Acoss the Envelope Membranes", Annu. Rev. Plant Physiol. Plant Mol. Biol., vol. 40, pp. 471–501 (no month identified 1989).

Koncz, C. and J. Schell, "The Promoter of $T_L$–DNA Gene 5 Controls the Tissue–specific Expresson of Chimaeric Genes Carried by a Novel Type of Agrobacterium Binary Vector", Mol. Gen. Genet., vol. 204, pp. 383–396 (no month identified 1986).

Koosha, F., R.H. Muller and S.S. Davis, "Polyhydroxybutyrate as a Drug Carrier", In Critical Reviews in Therapuetic Drg Carrier System, vol. 6, Issue 2, pp. 117–129 (no month identified 1989).

Kreuz, K. and H. Kleinig, "Synthesis of Prenyl Lipids in Cells of Spinach Leaf", Eur. J. Biochem,. vol. 141, pp. 531–535 (no month identified 1984).

Kung, S.D. and R. Wu, (eds), "Production of *Bacillus thuringiensis* Insecticidal Proteins in Plants", in Transgenic Plants, vol. 1, pp. 297–315 (no month identified 1993).

Laemmli, U.K., "Cleavage of Structural Proteins During the Assembly of the Head of Bateriophage T4", Nature, vol. 227, pp. 680–685 (Aug. 1970).

Lageveen, R.G., G.W. Huisman, H. Preusting, P. Ketelaar, G. Eggink and B. Witholt, "Formation of Polyesters by *Pseudomonas olevorans*: Effect of Substrates on Formation and Composition of Poly–(R)–3–Hydroxyalkanoates and Poly–(R)–3–Hydroxyalkenoates", Appl. Environ. Microbiol., vol. 54, No. 12, pp. 2924–2932 (Dec. 1988).

Lamppa, G.K., "The Chlorophyll a/b–binding Protein Inserts into the Thylakoids Independent of Its Cognate Transit Peptide", J. Biol. Chem., vol. 263, No. 29, pp. 14996–14999 (Oct. 1988).

Lloyd, A., A.R. Barnason, S.G. Rogers, M.C. Byrne, R.T. Fraley and R.B. Horsch, "Transformation of *Arabidopsis thaliana* with *Agrobacterium tumefaciens*", Science, vol. 234, pp. 464–466 (Oct. 1986).

Lubben, T.H., A.A. Gatenby, P. Ahlquist and K. Keegstra, "Chloroplast Import Characteristics of Chimeric Proteins", Plant Mol. Biol., Kluwer Academic Publishers, vol. 12, pp. 13–18 (no month identified 1989).

Lubben, T.H. and K. Keegstra, "Efficient in vitro Import of a Cytosolic Heat Shock Protein into Pea Chloroplasts", Proc. Natl. Acad. Sci., vol. 83, pp. 5502–5506 (Aug. 1986).

Lubben, T.H., S.M. Theq and K. Keegstra, "Transport of Proteins into Chloroplasts", Photosyn. Res., Kluwer Academic Publishers, vol. 17, pp. 173–194 (no month identified 1988).

Lundgren, D.G., R.M. Pfister and J.M. Merrick, "Structure of Poly–$\beta$–hydroxbutyric Acid Granules", J. Gen. Microbiol., vol. 34, No. 3, pp. 441–446 (May 1964).

Mahler, H.R., "Biological Oxidation of Fatty Acids", in Fatty Acids, Their Chemistry, Properties, Production and Uses, (Part 3, Markley, K.S.), R.E. Krieger Publishing, Chapter XV, pp. 1487–1550 (no month identified 1983).

Martin, J.H., W.H. Leonard and D.L. Stamp, (eds), "Crops of Other Plant Families", In Principles of Field Crop Prod., Chapter 36, pp. 898–932, Macmillan, New York (no month identified 1976).

Moffat, A.S., "High–Tech Plants Promise a Bumper Crop of New Products", Science, vol. 256, pp. 770–771 (May 1992).

Ostle, A.G. and J.G. Holt, "Nile Blue A as a Fluorescent Stain for Poly–$\beta$–hydroxybutyrate", Applied and Environmental Microbiology, vol. 44, No. 1, pp. 238–241 (Jul. 1982).

Pang, P.P., R.E. Pruitt and E.M. Meyerowitz, "Molecular Cloning, Genomic Organization, Expression and Evolution of 12S Seed Storage Protein Genes of *Arabidopsis thaliana*", Plant Mol. Biol., vol. 11, pp. 805–820 (no month identified 1988).

Peoples, O.P. and A. J. Sinskey, "Poly–$\beta$–hydroxybutyrate (PHB) Biosynthesis in *Alcaligenes eutrophus* H16", J. Biol. Chem., vol. 264, No. 26, pp. 15298–15303 (Sep. 15, 1989).

Peoples, O.P. and A.J. Sinskey, "Poly–$\beta$–hydroxybutyrate Biosynthesis in *Alcaligenes eutrophus* H16", J. Biol. Chem., vol. 264, No. 26, pp. 15293–15297 (Sep. 15, 1989).

Peoples, O.P. and A.J. Sinskey, "Fine Structural Analysis of the *Zoogloea ramigera* phbA–phbB Locus Encoding $\beta$–ketothiolase and Acetoacetyl–CoA Reductase: Nucleotide Sequence of phbB", Mol. Microbiol., vol. 3, No. 3, pp. 349–357 (Mar. 1989).

Peoples, O.P. and A.J. Sinskey, "Polyhydroxybutyrate (PHB): A Model System for Biopolymer Engineering: II", in Dawes, E.A. (ed) Proceedings of the NATO Advanced Research Workshop, pp. 191–202 (May 26–31, 1990).

Poirier, Y. and P. Jolicoeur, "Distinct Helper Virus Requirements for Abelson Murine Leukemia Virus–Induced Pre–B– and T–Cell Lymphomas", J. Virol., vol. 63, No. 5, pp. 2088–2098 (May 1989).

Poirier, Y., D.E. Dennis, C. Nawrath and C. Somerville, "Progress Toward Biologically Produced Biodegradable Thermoplastics", Adv. Mater., vol. 5, No. 1, pp. 30–36 (Jan. 1993).

Poirier, Y., E. Dennis, K. Klomparens and C. Somerville, "Polyhydroxybutyrate, a Biodegradable Thermoplastic, Produced in Transgenic Plants", Science, vol. 256, pp. 520–523 (Apr. 1992).

Poirier, Y., D.E. Dennis, K. Klomparens, C. Nawrath and C. Somerville, "Production of Polyhydroxybutyrate in Higher Plants", International Symposium on Bacterial Polyhydroxyalkanoates ISBP '92, Gottingen (Jun. 1–5, 1992) L17.

Poirier, Y., E. Dennis, K. Klomparens, C. Nawrath and C. Somerville, "Perspectives on the Production of Polyhydroxyalkanoates in Plants", FEMS Microbiol. Rev., vol. 103, pp. 237–246 (Dec. 1992).

Pool, R., "In Search of the Plastic Potato", Science, vol. 245, pp. 1187–1189 (Sep. 1989).

Potty, V.H., "Occurrence and Properties of Enzymes Associated with Mevalonic Acid Synthesis in the Orange", J. Food Sci., vol. 34, No. 3, pp. 231–234 (May/Jun. 1969).

Preiss, J., "Regulation of the Biosynthesis and Degradation of Starch", Ann. Rev. Plant Physiol., vol. 33, pp. 431–454 (no month identified 1982).

Pridmore, R.D., "New and Versatile Cloning Vectors With Kanamycin–resistance Marker", Gene, vol. 56, pp. 309–312 (no month identified 1987).

Proceedings of the Canadian Society of Plant Physiologists, University of Montreal (Dec. 13–15, 1992).

Puissant, C. and L.M. Houdebine, "An Improvement of the Single–step Method of RNA Isolation by Acid Guanidinium Thiocynate–Phenol–Chloroform Extraction", Bio Techniques, vol. 8, No. 2, pp. 148–149 (Feb. 1990).

Robinson, C. and R.J. Ellis, "Transport of Proteins into Chloroplasts", Eur. J. Biochem., vol. 142, pp. 343–346 (no month identified 1984).

Rogers, S.C. and A.J. Bendich, "Extraction of DNA from Plant Tissues", in Plant Molecular Biology Manual, Kluwer Academic Publishers, vol. A6, pp. 1–10 (no month identified 1988).

Sambrook, J., E.F. Fritsch and T. Maniatis, Molecular Cloning, A Laboratory Manual, 2nd. Edition, Cold Spring Harbor Laboratory Press, pp. 1.38–1.41, F.4–F.5, 1.63–1.71, 1.75, 6.15, 7.43–7.44, 7.49–7.52 and 9.52–9.55 (no month identified 1989).

Schiefelbein, J.W. and C.R. Somerville, "Genetic Control of Root Hair Development in *Arabidopsis thaliana*", Plant Cell, vol. 2, pp. 235–243 (Mar. 1990).

Schnell, D.J., G. Blobel and D. Pain, "Signal Peptide Analogs Derived from Two Chloroplast Precursors Interact with the Signal Recognition System of the Chloroplast Envelope", J. Biol. Chem., vol. 266, No. 5, pp. 3335–3342 (Feb. 1991).

Schreier, P.H., E.A. Seftor, J. Schell and H.J. Bohnert, "The Use of Nuclear–encoded Sequences to Direct the Light–regulated Synthesis and Transport of a Foreign Protein into Plant Chloroplasts", EMBO J., vol. 4, No. 1, pp. 25–32 (Jan. 1985).

Schubert, P., A. Steinbüchel and H.G. Schlegel, "Cloning of the *Alcaligenes eutrophus* Genes for Synthesis of Poly–β–Hydroxybutyric Acid (PHB) and Synthesis of PHB in *Escherichia coli*", J. Bacteriol., vol. 170, No. 12, pp. 5837–5847 (Dec. 1988).

Schultz, G. and D. Schulze–Siebert, "On the Origin of Isoprenoid Intermediates for the Synthesis of Plastoquinone–9 and β–Carotene in Developing Chloroplasts", in Biological Role of Platn Lipid, P.A. Biacs, K. Gruiz and T. Kremmer (eds), Plenum Publ. Corp., New York, NY, pp. 313–319 no month identified 1989).

Senior, P.J. and E.A. Dawes, "The Regulation of Poly–β–hydroxybutyrate Metabolism in *Azotobacter beijerinckii*", Biochem. J., vol. 134, No. 1, pp. 225–238 (May 1973).

Seymour, G.B., R.G. Fray, P. Hill and G.A. Tucker, "Down–regulation of Two Non–homologous Endogenous Tomato Genes with a Single Chimaeric Sense Gene Construct", Plant Mol. Biol., vol. 23, pp. 1–9 (Month 1993).

Slater, S.C., W. H. Voige and D.E. Dennis, "Cloning and Expression in *Escherichia coli* of the *Alcaligenes eutrophus* H16 Poly–β–Hydroxybutyrate Biosynthetic Pathway", J. Bacteriol., vol. 170, No. 10, pp. 4431–4436 (Oct. 1988).

Southern, E.M., "Detection of Specific Sequences Among DNA Fragments Separated by Gel Electrophoresis", J. Mol. Biol., vol. 98, pp. 503–517 (Nov. 1975).

Steinbüchel, A., E. Hustede, M. Liebergesell, U. Pieper, A. Timm and H. Valentin, "Molecular Basis for Biosynthesis and Accumulation of Polyhydroxyalkanoic Acids in Bacterial", FEMS Microbiol. Rev., vol. 103, No. 2/4, pp. 217–230, (Dec. 9, 1992).

Steinbüchel, A. and H.G. Schlegel, "Physiology and Molecular Genetics of Poly(β–hydroxyalkanoic acid) Synthesis in *Alcaligenes eutrophus*", Mol. Microbiol., vol. 5, No. 3, pp. 535–542 (Mar. 1991).

UC Davis–Pacific Rim Food and Agricultural Biotechnology Conference Series, "Genetic Engineering of a Unique Biopolymer Polyhydroxybutyrate", (Jun. 20–24, 1992).

Valvekens, D., M. Van Montagu and M. Van Lijsebettens, "*Agrobacterium tumefaciens*–mediated Transformation of *Arabidopsis thaliana* Root Explants by Using Kanamycin Selection", Proc. Natl. Acad. Sci. USA, vol. 85, pp. 5536–5540 (Aug. 1988).

van de Broeck, G., M.P. Timko, A.P. Kausch, A.R. Cashmore, M. Van Montagu and L. Herrera–Estrella, "Targeting of a Foreign Protein to Chloroplasts by Fusion to the Transit Peptide from the Small Subunit of Ribulose 1,5–bisphosphate Carboxylase", Nature, vol. 313, pp. 358–363 (Jan. 1985).

Wallen, L.L. and W.K. Rohwedder, "Poly–β–hydroxyalkanoate from Activated Sludge", Environ. Sci. Technol., vol. 8, No. 6, pp. 576–579 (Jun. 1974).

Wasmann, C.C, R. Reis, S.G. Barlett and H.J. Bohnert, "The Importance of the Transit Peptide and the Transported Protein for Protein Import into Chloroplasts", Mol. Gen. Genet., vol. 205, pp. 446–453 (no month identified 1986).

Witholt, B., G.W. Huisman and H. Preusting., "Bacterial Poly(3–hydroxyalkanoates)", Proceedings of the NATO Advanced Research Workshop, pp. 161–173 (May 26–31, 1990).

Zambryski, P., H. Joos, C. Genetello, J. Leemans, M. Van Montagu and J. Schell, "Ti Plasmid Vector for the Introduction of DNA into Plant Cells Without Alteration of their Normal Regeneration Capacity", EMBO, vol. 2, No. 12, pp. 2143–2150 (Dec. 1983).

Anderson, A. and Dawes, E. A., Microbiol. Rev. 54:450–472 (1990).

Wallen, L. L. and Rohwedder, W. K., Environ. Sci. Technol. 8:576–579 (1974).

Holmes, P. A., Phys. Technol. 16:32–36 (1985).

Slater, S.C., et al, J. Bacteriol. 170:4431–4436 (1988).

Schubert, P., et al., J. Bacteriol. 170:5837–5847 (1988).

Janes, B. B., et al., In Dawes, E. A. (ed) Novel Biodegradable Microbial Polymers, Kluwer Academic Publishers, pp. 175–190 (1990).

Peoples, O. P. and Sinskey, A. J., J. Biol. Chem. 264:15293–15297 (1989).

Peoples, O. P. and Sinskey, A. J., J. Biol. Chem. 264:15298–15303 (1989).

Benfey, P. N. and Chua, N. H. Science 250: 959–966 (1990).

Valvekens, D. et al., Proc. Natl. Acad. Sci. USA 85:5536–5540 (1988).

Senior, P. J. and Dawes, E. A., Biochem. J. 134:225–238 (1973).

Lundgren, D. G., Pfister, R. M. and Merrick, J. M., J. Gen. Microbiol. 34:441–446 (1964).

Sambrook, J., Fritsch, E. F. and Maniatis, T., Molecular Cloning, a laboratory manual, Cold Spring Harbor Laboratory Press (1989).

Hanahan, D., J. Mol. Biol. 166:557–580 (1983).

Zambryski, P. et al., EMBO 2:2143–2150 (1983).

Estelle, M. A. and Somerville, C., Mol. Gen. Genet. 206:200–206 (1987).

Schiefelbein, J. W. and Somerville, C. R., Plant Cell 2:235–243 (1990).

Rogers, S. C. and Bendich, A. J., Plant Molecular Biology Manual A6:1–10 (1988).

Southern, E. M., J. Mol. Biol. 38:503–517 (1975).

Sambrook, J., Fritsch, E. F. and Maniatis, T., Molecular Cloning, a laboratory manuel Cold Spring Harbor Laboratory Press (1989) (AS–5).

Feinberg, A. P. and Volgelstein, B., Anal. Biochem. 136:6–13 (1983).

Poirier, Y. and Jolicoeur, P., J. Virol. 63: 2088–2098 (1989).

Puissant, C. and Houdebine, L. M., BioTechniques 8:148–149 (1990).

| Restriction Enzymes | Enumeration from SEQ ID NO:1 | Nucleotide Sequences from SEQ ID NO:1 |
|---|---|---|
| DdeI | 175-179 | CTGAG |
| BstBI | 809-814 | TTCGAA |
| DdeI | 1078-1082 | CTCAG |
| PstI | 1604-1609 | CTGCAG |
| PstI | 2177-2182 | CTGCAG |
| PstI | 2657-2662 | CTGCAG |
| Tth111I | 2702-2710 | GACGTTGTC |
| DdeI | 3956-3960 | CTCAG |
| Tth111I | 4168-4176 | GACAAGGTC |
| Tth111I | 4516-4524 | GACATGGTC |
| DdeI | 4892-4896 | CTTAG |
| PstI | 4975-4980 | CTGCAG |

FIG. 2

TRANSGENIC PLANTS PRODUCING POLYHYDROXYALKANOATES

This is a continuation of application Ser. No. 07/732,243, filed on Jul. 19, 1991, now abandoned.

FIELD OF THE INVENTION

This invention concerns the introduction and expression of certain genetic informational material, i.e., DNA which includes genes coding for proteinaceous materials and/or genes regulating or otherwise influencing the production thereof, into cells of higher plants and the regeneration of fertile plants from the genetically transformed cells. The purpose of this genetic intervention is to transfer to higher plants, from microbial organisms, the ability to synthesize polymeric materials composed of linear polyesters of hydroxy acids. This class of materials is generally referred to as polyhydroxyalkanoates. The specific example shown here is the production of polyhydroxybutyrate (PHB).

BACKGROUND OF THE INVENTION

Many species of bacteria accumulate granules of polyesters composed of hydroxyacyl monomers which serve as carbon reserves. The occurrence, metabolism, metabolic role, and industrial uses of bacterial polyhydroxyalkanoates has recently been reviewed (Anderson, A. and Dawes, E. A., Microbiol. Rev. 54:450–472 (1990)). The most commonly found compound of this class is poly(D(–)-3-hydroxybutyrate). However, some species accumulate copolymers of different hydroxyalkanoates such as 3-hydroxypentaneoate (Wallen, L. L. and Rohwedder, W. K., Environ. Sci. Technol. 8:576–579 (1974)). At least 11 short-chain 3-hydroxyacids are found as components of polymers from marine sediments. Studies of polyhydroxyalkanoate production in *Alcaligenes eutrophus* have shown that when the bacteria are cultivated in a medium with only glucose as a carbon source, only PHB is accumulated. However, when both glucose and propionic acid are provided as carbon sources, the bacteria accumulates random copolymers of 3-hydroxypentanoate and 3-hydroxybutyrate (Holmes, P. A., Phys. Technol. 16:32–36 (1985); Holmes, P. A., Wright, L. F. and Collins, S. H. European Patents 0 069 497, January 1983 and 0 052 459, December 1985). In addition, when *A. eutrophus* is supplied with various other carbon sources, polyesters containing 4-hydroxybutyrate and 5-hydroxyvalerate monomers are produced (Table I in Anderson, A. J. and Dawes, A. E., Microbiol. Rev. 54:450–472 (1990)). Thus, it appears that the composition of the polymer is regulated to some extent by the availability of alternative substrates for the enzymes which catalyzed synthesis of the polymer from monomers.

PHB accumulates in bacterial cells as granules of approximately 0.24 to 0.5 μm in diameter. On the basis of measurements of the molecular weight of PHB monomers, each granule has been estimated to contain a minimum of 1,000 polymer chains. The granules have been proposed to possess a membrane coat composed of lipid and protein representing approximately 0.5 and 2%, respectively, of the granule weight (Anderson, A. and Dawes, E. A., Microbiol. Rev. 54:450–472 (1990)). The activity of the PHB synthase enzyme is thought to be associated with this membrane. The state of the PHB within the granule is a matter of substantial uncertainty. Recent evidence suggests that the polymer within the granules is in an amorphous state. It is not known what regulates the size of PHB granules in any organism.

In most organisms, PHB is synthesized from acetyl coenzyme A (acetyl-CoA) by a sequence of three reactions catalyzed by 3-ketothiolase (acetyl-CoA acetyltransferase; EC 2.3.1.9), acetoacetyl-CoA reductase (hydroxybutyryl-CoA dehydrogenase; EC 1.1.1.36) and poly(3-hydroxybutyrate)synthase. The pathway is shown in FIG. 1. In *Rhodospirillum rubrum*, PHB is synthesized by conversion of L(+)-3-hydroxybutyryl-CoA to crotonyl-CoA to D(–)-3-hydroxybutyryl-CoA. The 3-ketothiolase has been purified from various PHB-synthesizing bacteria and has been studied in several species of higher plants. The role of the enzyme in higher plants is thought to be in the production of acetoacetyl-CoA for mevalonate production as well as in the degradation of fatty acids. The acetoacetyl-CoA reductase has been detected in a number of PHB-synthesizing bacteria. Several species, including *A. eutrophus*, appear to have two isoenzymes which differ with respect to substrate specificities and cofactor requirements. The NADH reductase of *A. eutrophus* is active with C4 to C10 D(–)- and L(+)-3-hydroxyacyl-CoAs, whereas the NADPH reductase is active with only C4 and C5 D(–)-3-hydroxyacyl-CoAs. An enzyme of this kind has never been reported in higher plants. PHB synthase activity has been detected in PHB-accumulating bacteria as both a soluble enzyme and as a granule-bound activity, depending on the growth conditions. Both forms of the enzyme have been partially purified but have not as yet been purified to homogeneity because of instability. The PHB synthases of *A. eutrophus* is specific for D(–)-enantiomers and when tested with 3-hydroxyacyl-CoAs, was shown to be active only with C4 and C5 substrates, consistent with the observation that only C4 and C5 3-hydroxyacid monomer units are incorporated into the polymer by this organism. The mechanism of PHB synthase action remains obscure. It is presumed that the chain transfer role played by the synthase must in some way control the molecular weight of the polymer produced, which is characteristic of a given organism. PHB synthase activity has never been reported in any plant.

Several groups of researchers have independently cloned, and expressed in *E. coli*, the genes involved in the biosynthesis of PHB by *A. eutrophus* (Slater, S.C., et al., J. Bacteriol. 170:4431–4436 (1988); Schubert, P., et al., J. Bacteriol. 170:5837–5847 (1988)). Recombinant strains of *E. coli* carrying a 5.2 kbp fragment from *A. eutrophus* were capable of accumulating substantial quantities of PHB as intracellular granules. The nucleotide sequence of the 5.2 kbp fragment was also independently determined by two groups (Janes, B. B., et al., In Dawes, E. A. (ed) Novel Biodegradable Microbial Polymers, Kluwer Academic Publishers, pp 175–190 (1990); Peoples, O. P. and Sinskey, A. J., J. Biol. Chem. 264:15293–15297 (1989); Peoples, O. P. and Sinskey, A. J., J. Biol. Chem. 264:15298–15303 (1989)). Analysis of the deduced amino acid sequences of the open reading frames, in conjunction with evidence based on genetic complementation studies, revealed that the 5.2 kbp fragment contained three closely linked genes encoding the three enzymes required for PHB production. A patent concerning the use of the cloned genes to overproduce the biosynthetic enzymes in bacteria has been filed (Peoples, O. P. and Sinskey, A. J., Int Patent WO 89/00202, January 1989).

Certain species of bacteria have the ability to excrete enzymes and degrade PHB and related polyhydroxyalkanoates (Reviewed in Anderson, A. and Dawes, E. A., Microbiol. Rev. 54:450–472 (1990)). Because of the prevalence of these bacterial species in many natural environments, PHB is rapidly degraded in soil and activated sludge. Thus, PHB and related polyhydroxyalkanoates are of interest as renewable sources of biodegradable thermoplastic. Industrial PHB production from large-scale cultivation of bacteria began in 1982. The PHB produced in this way is marketed by ICI plc under the trade name Biopol. However, because of the costs associated with growing and harvesting large cultures of bacteria, the PHB is much more costly to produce than polymeric materials such as starch which are accumulated to high levels in many species of higher plants. Therefore, it may be advantageous to develop, by genetic engineering, lines of higher plants which accumulate PHB.

BRIEF DESCRIPTION OF FIGURES

SEQ ID NO:1 shows the nucleotide sequence of the PHB operon from A. eutrophus. The sequence was obtained from Janes, B., Hollar, J. and Dennis, D. in Dawes, E. A. (ed), Novel Biodegradable Polymers, Kluwer Academic Publishers, 175–190 (1990). The open reading frame from nucleotide 842 to 2611 encodes the PHB synthase (phbC gene) (amino acids S1 to S589). The open reading frame from nucleotide 2696 to 3877 encodes the enzyme 3-ketothiolase (phb A gene) (amino acid T1 to T393). The open reading frame from nucleotide 3952 to 4692 encodes the enzyme acetoacetyl-CoA reductase (phb B gene) (amino acid R1 to R246). FIG. 2 shows the sequences for the restriction enzymes DdeI, BstBI, PstI, SacI and TthIIII. These restriction enzymes were used in the subcloning of the phb genes.

FIG. 10B shows higher magnification of the nucleus of the upper right cell shown in FIG. 10A. FIG. 10C shows the nucleus of a leaf mesophyll cell from a RedB-2D X S8-1-2A E1 hybrid showing an agglomeration of granules. FIG. 10D show the leaf mesophyll cell from a RedB-2A X S8-1-2A F1 hybrid showing electron-lucent granules in the nucleus (N) and vacuole (V). FIG. 10E shows the leaf mesophyll cell from a Red B-2A X S8-1-2A F1 hybrid showing electron-lucent granules in the cytoplasm. FIG. 10F show the cotyledon cells from a RedB-2A X S8-1-2C F1 hybrid seed showing granules in the nucleus. Arrows indicate agglomerations of electron-lucent granules. Bar=1 µm for FIGS. 10A to 10F. Bar=0.25 µm for FIG. 10E.

SUMMARY OF THE INVENTION

Figure 1:
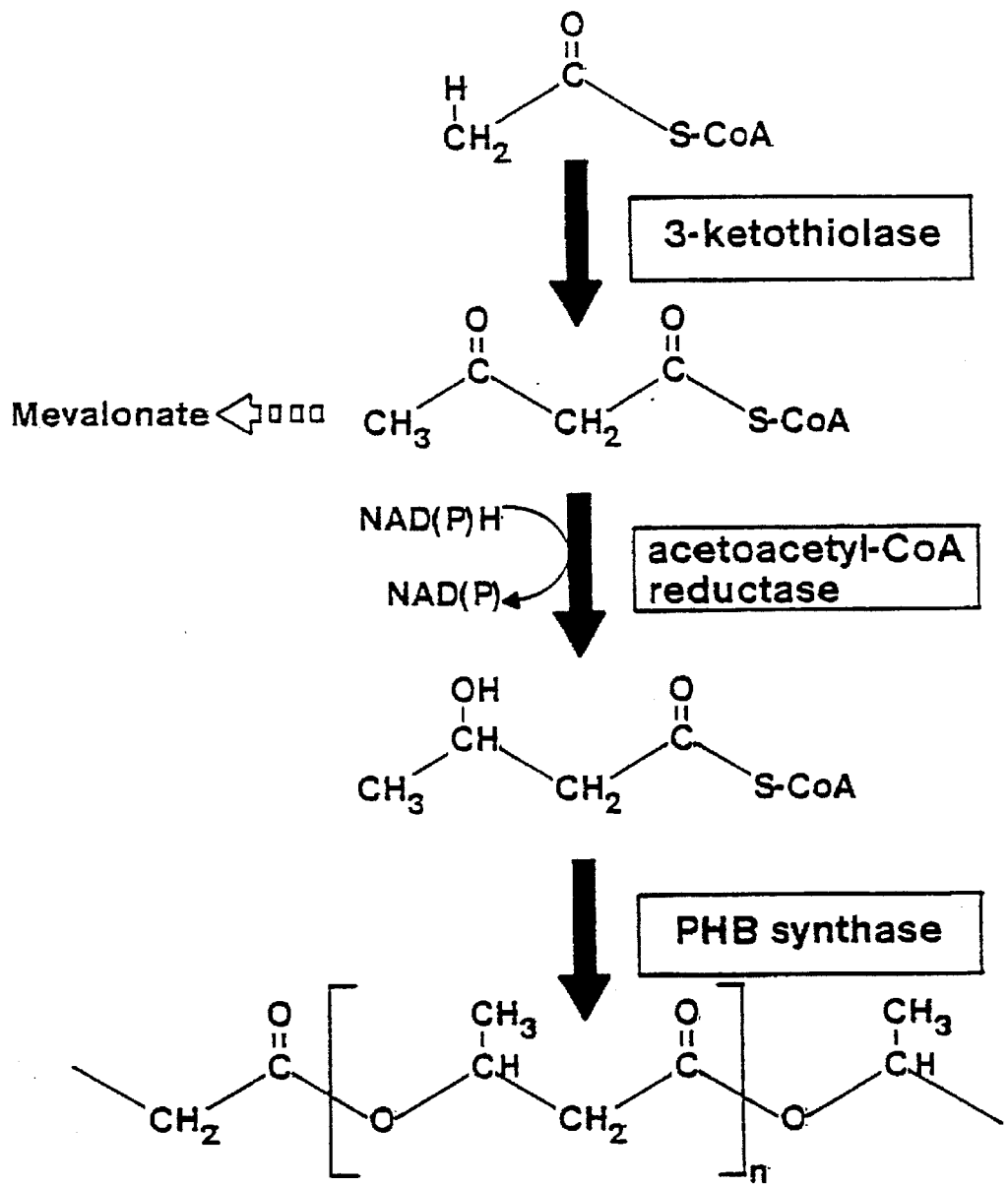
FIG. 1 shows the biochemical pathway for the production of polyhydroxybutyrate (PHB). In A. eutrophus, PHB is produced by the successive action of three enzymes: 3-ketothiolase, converting acetyl-CoA to acetoacetyl-CoA; acetoacetyl-CoA reductase, converting acetoacetyl-CoA to D(–)-3-hydroxybutyryl-CoA; PHB synthase, converting D(-1-3-hydroxybutyryl-CoA to polyhydroxybutyrate. In plants and animals, acetoacetyl-CoA is a precursor in the production of mevalonate.

The present invention relates to a transgenic plant material containing foreign DNA leading to the production of a polyhydroxyalkanoate.

The present invention further relates to a transgenic plant material containing foreign DNA encoding a peptide which exhibits 3-ketothiolase activity.

The present invention also relates to a transgenic plant material containing foreign DNA encoding a peptide which exhibits acetoacetyl-CoA reductase activity.

The present invention also relates to a transgenic plant material containing foreign DNA encoding a peptide which exhibits foreign PHB synthase activity.

The present invention relates to a method for introducing bacterial DNA encoding proteins required for the synthesis of a polyhydroxyalkanoate into a plant, which comprises mating by sexual fertilization two plants, which do not produce PHB, each containing foreign DNA encoding one or more different enzymes in a pathway leading to polymerization of hydroxyacyl-CoA by polyhydroxyalkanoate synthase to produce a plant encoding the polyhydroxyalkanoate.

Thus, the present invention provides a method for producing genetically modified higher plants which produce and accumulate PHB or related polyhydroxyalkanoates. In one embodiment, PHB-producing plants are obtained by stably introducing bacterial genes which encode the enzymes acetoacetyl-CoA reductase (hydroxybutyryl-CoA dehydrogenase) and poly(3-hydroxybutyrate) synthase into the plants by Ti-plasmid mediated transformation. Because bacterial genes are not normally transcribed in plant cells, the genes are modified so that they are under transcriptional control of a DNA sequence (i.e., a "promoter") which induces trancription in plant cells. The genes are also modified by the addition of an appropriate DNA sequence to the non-coding 3'-region of the genes so that the transcripts produced in plant cells are appropriately polyadenylated.

In one embodiment of the invention, PHB-producing plants are obtained by sexual crosses between two parental lines which do not produce PHB. This is accomplished by cross-pollinating a transgenic plant line homozygous for ectopic copies of a modified PHB synthase gene with a transgenic plant line homozygous for ectopic copies of a modified acetoacetyl-CoA reductase gene. In this context, the term "ectopic genes" refers to genes which are not normally present in an organism but have been stably integrated into the genome by genetic transformation. To be homozygous for ectopic copies means that, in a diploid organism, both homologous chromosomes have the ectopic gene integrated at the same location within the chromosome.

DETAILED DESCRIPTION OF THE INVENTION

Prior to setting forth the invention, it is helpful to set forth definitions of certain terms to be used hereinafter.

Transformation means the process for changing the genotype of a recipient organism by the stable introduction of DNA by whatever means.

A transgenic plant is a plant which contains DNA sequences which are not normally present in the species, but were introduced by transformation.

Transcription means the formation of an RNA chain in accordance with the genetic information contained in the DNA.

Translation means the process whereby the genetic information in an mRNA molecule directs the order of specific amino acids during protein synthesis.

A promoter is a DNA fragment which causes transcription of genetic material. For the purposes described herein, promoter is used to denote DNA fragments that permit transcription in plant cells. The CaMV 35S-promoter is a DNA fragment from the cauliflower mosaic virus that causes relatively high levels of transcription in many different tissues of many species of higher plants (Benfey, P. N. and Chua, N. H. Science 250:959–966 (1990)).

A poly-A addition site is a nucleotide sequence which causes certain enzymes to cleave mRNA at a specific site and to add a sequence of adenylic acid residues to the 3'-end of the mRNA.

phbC, phbA, phbB are the gene symbols given to the A. eutrophus genes for PHB synthase, 3-ketothiolase and acetoacetyl-CoA reductase, respectively (Peoples, O. P. and Sinskey, A. J., J. Biol. Chem. 264:15298–15303 (1989)).

In describing the progeny of transgenic plants, it is useful to adopt a convention which designates how many generations of self-pollination have elapsed since the introduction of DNA. Herein, we designate the original transformant the T0 generation. The progeny resulting from self-pollination of this generation is designated the T1 generation and so on.

In the case of cross-pollination between two distinct parental plants, the resulting progeny from the initial cross-pollination event is designated the F1 generation.

Although the experiments discussed hereinafter concern the plant species Arabidopsis thaliana (L.) the process described is generally applicable to any higher plant for which a method of transformation is available. Similarly, although the process described herein concerns the use of genes from A. eutrophus, the process described is generally applicable to the use of genes from any organism which is capable of synthesis of PHB. It is also clear that, although the process described concerns the production of PHB, the procedure is generally applicable to the production of any polyhydroxyalkanoate which is normally produced in microorganisms by the activity of polyhydroxyalkanoate (PHA) synthase (which includes PHB synthase), and for which the appropriate hydroxyacyl-CoA substrate is produced in the particular plant.

EXPERIMENTAL DETAILS

Experimental Design

The production of PHB in progeny of transformed plants requires the completion of a sequence of steps as follows: (1) the construction of a series of bacterial plasmids containing promoter fusions, (2) the transfer of these plasmids into Agrobacterium tumefaciens, (3) the use of A. tumefaciens to introduce the genes into cells of the plant (i.e., A. thaliana in this example), (4) the regeneration of transgenic plants (5) the selection of plants which are homozygous for the ectopic genes (6) analysis of the function of the ectopic genes in the transformed plants to ensure that they are expressed and that the gene products are functional (7) the production of hybrid plants containing two or more different ectopic genes by sexual crosses, (8) the analysis of the hybrid material for the presence of PHB. These steps are described in detail in the following sections.

Construction of Transcriptional Fusions

In order to obtain transcription of the bacterial genes in higher plants, the bacterial genes must be modified by the addition of a plant promoter so that they are transcribed when introduced into higher plants. In addition, it is common practice to add a poly-A addition site to the 3'region of bacterial genes in order to obtain proper expression of the genes in higher plants. Both of these requirements were satisfied by cloning the phbC, phbA and phbB genes from plasmid pTZ18U-PHB into the binary Ti plasmid vector pBI121 (Clonetech, CA). The nucleotide sequence of the phbC, phbA and phbB genes contained within the plasmid pTZ18U-PHB is shown in SEQ ID NO:1. The relevant restriction enzyme sites used in the subclosing of the phb genes is shown in FIG. 2.

A CaMV 35S-phbA gene fusion was constructed by digesting the plasmid pTZ18U-PHB with restriction enzymes PstI and DdeI. The 1.3 kb restriction fragment containing the coding sequence of the 3-ketothiolase gene was separated from other DNA fragments by agarose gel electrophoresis. The DNA fragment was recovered from the agarose using a DEAE cellulose membrane (Schleicher & Schuell NA-45 DEAE membrane). The staggered ends of the DNA fragment were filled-in by incubating the purified restriction fragment with T4 DNA polymerase and deoxynucleotide triphosphates. The blunt fragment was then cloned into the SmaI site in plasmid pUC18 to produce the plasmid pUC-THIO. The 1.3 kb restriction fragment was excised from pUC-THIO plasmid by digestion with BamHI and SacI, purified by electrophoresis using a DEAE cellulose membrane and ligated into plasmid pBI121 which had been previously digested with the same two enzymes. The resulting plasmid, designated pBI-THIO, was found to have the *A. eutrophus* 3-ketothiolase gene in the correct orientation, relative to the CaMV 35S promoter and poly-A addition site of pBI121, so that it would be expected to be expressed in higher plants. A schematic summary of the steps involved in construction of pBI-THIO is presented as FIG. 3.

A CaMV 35S-phbC gene fusion was constructed by digesting the plasmid pTZ18U-PHB with restriction enzymes BstBI and TthIIII. The 1.9 kb restriction fragment containing the coding sequence of the PHB synthase gene was separated from other DNA fragments by agarose gel electrophoresis. The DNA fragment was recovered from the agarose using a DEAE cellulose membrane. The staggered ends of the DNA fragment were filled in by incubating the purified restriction fragment with T4 DNA polymerase and deoxynucleotide triphosphates. The blunt fragment was then cloned into the SmaI site in plasmid pUC18 to produce plasmid pUC-SYN. The 1.9 kb restriction fragment was excised from pUC-SYN by complete digestion with BamHI and partial digestion with SacI, purified by electrophoresis using DEAE cellulose membranes and ligated into plasmid pBI121 which had been previously digested with the same two enzymes. The resulting plasmid, designated pBI-SYN, was found to have the *A. eutrophus* PHB synthase gene in the correct orientation, relative to the CaMV 35S promoter and poly-A addition site of pBI121, so that it would be expected to be expressed in higher plants. A schematic summary of the steps involved in construction of pBI-SYN is presented in FIG. 4.

A CaMV 35S-phbB gene fusion was constructed by using a pair of synthetic oligonucleotides for primers in a polymerase chain reaction (PCR) to amplify the phbB gene from plasmid pTZ18U-PHB. The sequence of the oligonucleotide primers is presented in FIG. 5 where they are designated PCR primer #1 and PCR primer #2. The oligonucleotides were designed in such a way that the amplified DNA sequence contained a synthetic BamHI site near the 5'-end of the coding sequence and a synthetic KpnI site at the 3'-end of the sequence. The 790 base pair product of the polymerase chain reaction was separated and purified from agarose gel, restricted with BamHI and KpnI and ligated into plasmid pUC18, which was previously restricted with the same two enzymes, to produce plasmid pUC-RED. The restriction fragment was excised from pUC-RED by digestion with BamHI and SacI, purified by electrophoresis using a DEAE cellulose membrane and ligated into plasmid pBI121 which had been previously digested with the same two enzymes. The resulting plasmid, designated pBI-RED, was found to have the *A. eutrophus* acetoacetyl-CoA reductase gene in the correct orientation, relative to the CaMV 35S promoter and poly-A addition site of pBI121, so that it would be expected to be expressed in higher plants. A schematic summary of the steps involved in construction of pBI-RED is presented as FIG. 5.

The plasmids pBI-SYN, pBI-THIO and pBI-RED were transferred into *Agrobacterium tumefaciens* strain C58 pGV3850 by electroporation. Plasmid containing colonies were recovered by selection for expression of the kanamycin resistance gene present on the parental plasmid pBI121.

Production of Transgenic Plants

Cells of *A. thaliana* were transformed by incubating sterile root tissue with cultures of *A. tumefaciens* carrying the recombinant binary Ti plasmids described in the previous section. Roots from sterile seedlings of *A. thaliana* race Rschew were transformed as described by Valvekens, D. et al., Proc. Natl. Acad. Sci. USA 85:5536–5540 (1988). Each of the three strains of *A. tumefaciens* carrying one of the modified phb genes was used to infect *A. thaliana* root pieces. This resulted in the recovery of approximately 50 kanamycin resistant callus tissues in each case. Of these, 10–25% gave rise to fertile shoots which produced seeds. Each plant which produced seeds was assigned a different number to indicate that it represented a distinct transformation event.

A total of 11 putative transgenic plants were recovered from tissues treated with *A. tumefacienes* carrying the plasmid pBI-RED. These designated RedB-2A, -2B, -2C, -2D, -2E, -2F, -2G, -2H, -3A, -5A and RedD-3A. All these transgenic plant lines, except RedB-2F, -2H and -5A, were analyzed in detail as described in the following sections.

A total of 5 putative transgenic plants were recovered from tissues treated with *A. tumefacienes* carrying the plasmid pBI-THIO. These were designated T3-2A, T4-2A, T4-3A, T4-3B and T4-3C. All these transgenic plant lines, except T4-3C, were analyzed in detail as described in the following sections.

A total of 4 putative transgenic plants were recovered from tissue treated with *A. tumefacienes* carrying the plasmid pBI-SYN. These were designated S8-1-2A, S8-1-2C, S12-3A and SSPUC-2A. All these trangenic plant lines were analyzed in detail as described in the following sections.

The presence of T-DNA in the putative transgenic plants was verified by sowing seed from the transgenic plants on agar-solidified mineral medium containing 50 μg/ml of kanamycin. This concentration of kanamycin prevents the growth of untransformed *A. thaliana* plants but permits plants containing the NPTII gene carried on pBI121 or pBI121-derived plasmids to grow normally. The seeds from transgenic plants T4-2A, RedD-3A and S8-1-2A are available from The American Type Culture Collection, Rockville, MD 20852.

Isolation of Putative Homozygous Transgenic Lines

A minimum criterion used to produce homozygous transgenic lines was that all the progeny from an homozygous plant are expected to be kanamycin resistant. Because the presence of multiple ectopic copies of the NPTII gene from pBI121 at different locations in the genome may cause a similar phenotype, this criterion is most useful when the primary transformation event involves insertion of T-DNA into only one chromosomal location.

In order to identify putative homozygous lines, several kanamycin resistant T1 plants from each transgenic line were grown to maturity in reproductive isolation. The frequency of kanamycin resistance was then determined in samples of approximately 50 T2 seed from each line. If all of the T2 seed from a particular plant were kanamycin resistant, the line was provisionally considered to be homozygous.

Analysis of the Integration of the phb Genes in Transgenic Plants

Figure 3:
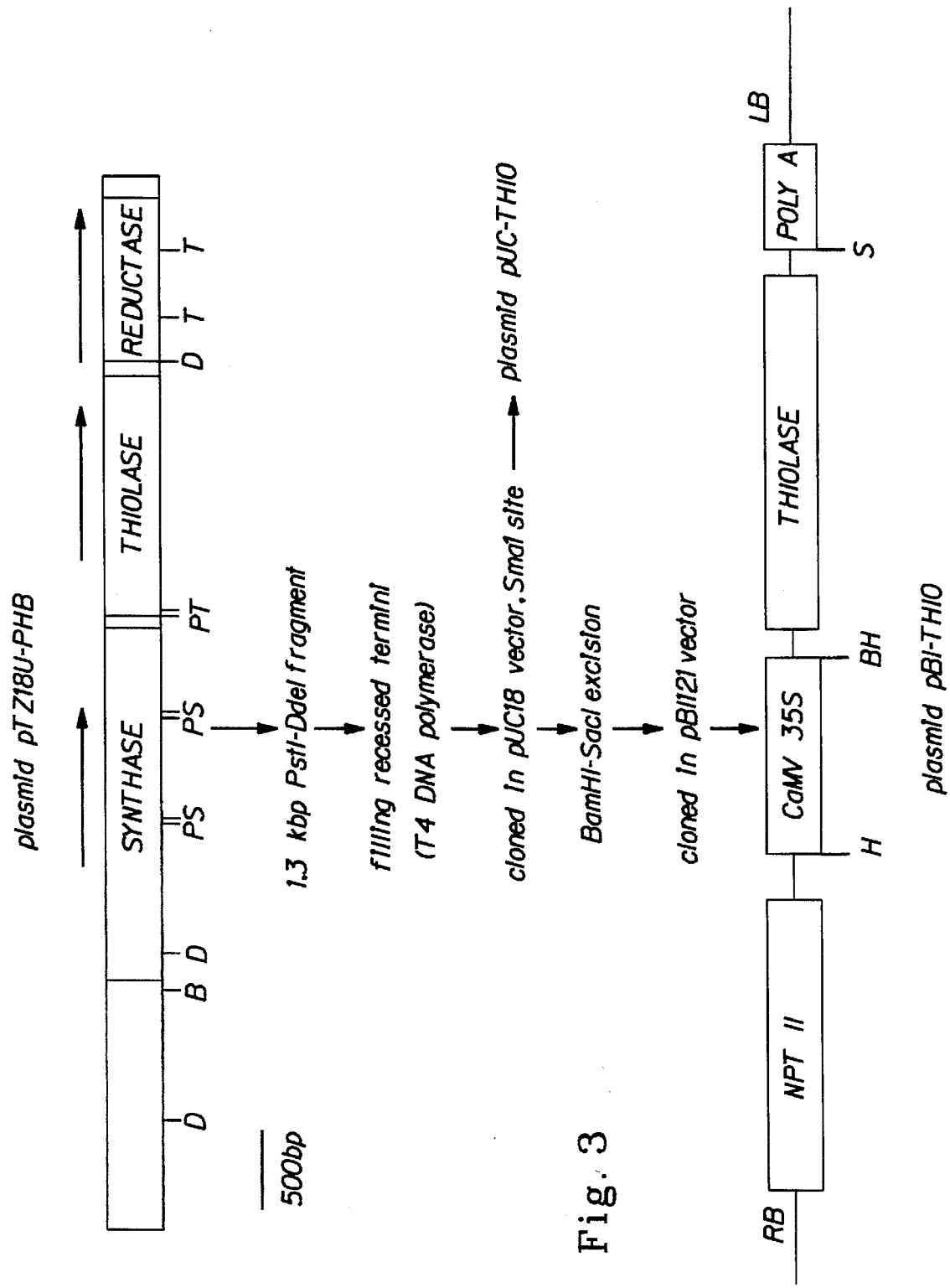
FIG. 3 shows a schematic summary of the steps involved in the construction of plasmids pUC-THIO and pBI-THIO. The purpose of this latter plasmid is to place the 3-ketothiolase gene from A. eutrophus under transcriptional control of the CaMV 35S promoter so that it will be transcribed in higher plants. The top diagram represent the A. eutrophus PHB operon with the approximate location of the open reading frames encoding the PHB synthase, 3-ketothiolase and acetoacetyl-CoA reductase. The horizontal arrows indicate the direction of transcription. The bottom diagram indicates the major components of the pBI121-derived plasmids: NPT II, neomycin phosphotransferase II gene encoding kanamycin resistance; CaMV 35S, cauliflower mosaic virus 35S promoter; poly A, polyadenylation sequence; RB, right border sequence of T-DNA; LB, left border sequence of T-DNA. The bottom diagram is not drawn to scale. Abbreviations for restriction enzyme sites: D, DdeI; P, PstI; B, BstBI; T, TthIIII; BH, BamHI; S, SacI; H, HindIII.
Figure 4:
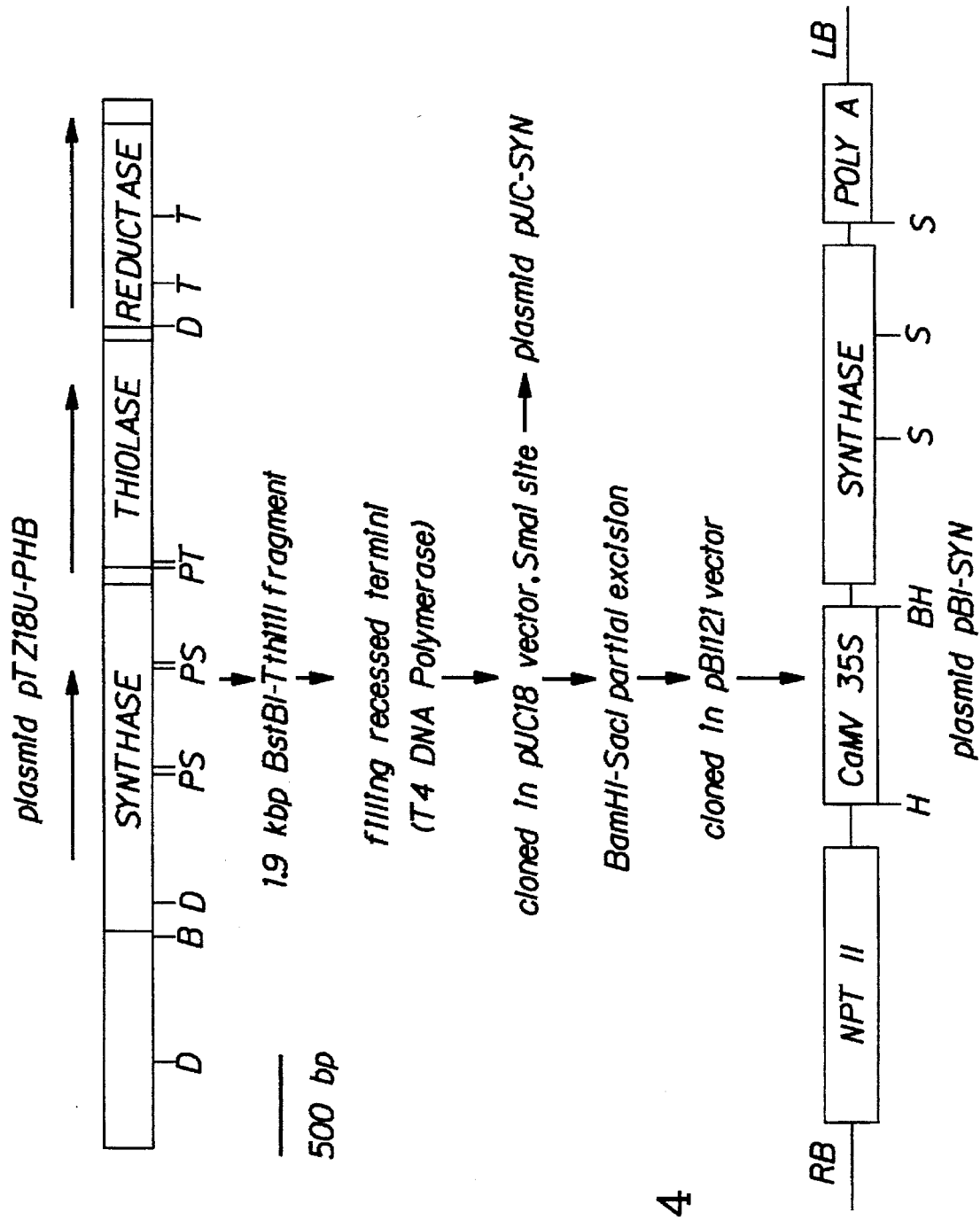
FIG. 4 shows a schematic summary of the steps involved in construction of plasmid pUC-SYN and pBI-SYN. The purpose of this latter plasmid is to place the PHB synthase gene from A. eutrophus under transcriptional control of the CaMV 35S promoter so that it will be transcribed in higher plants. Diagrams and abbreviations are described in FIG. 3.
Figure 5:
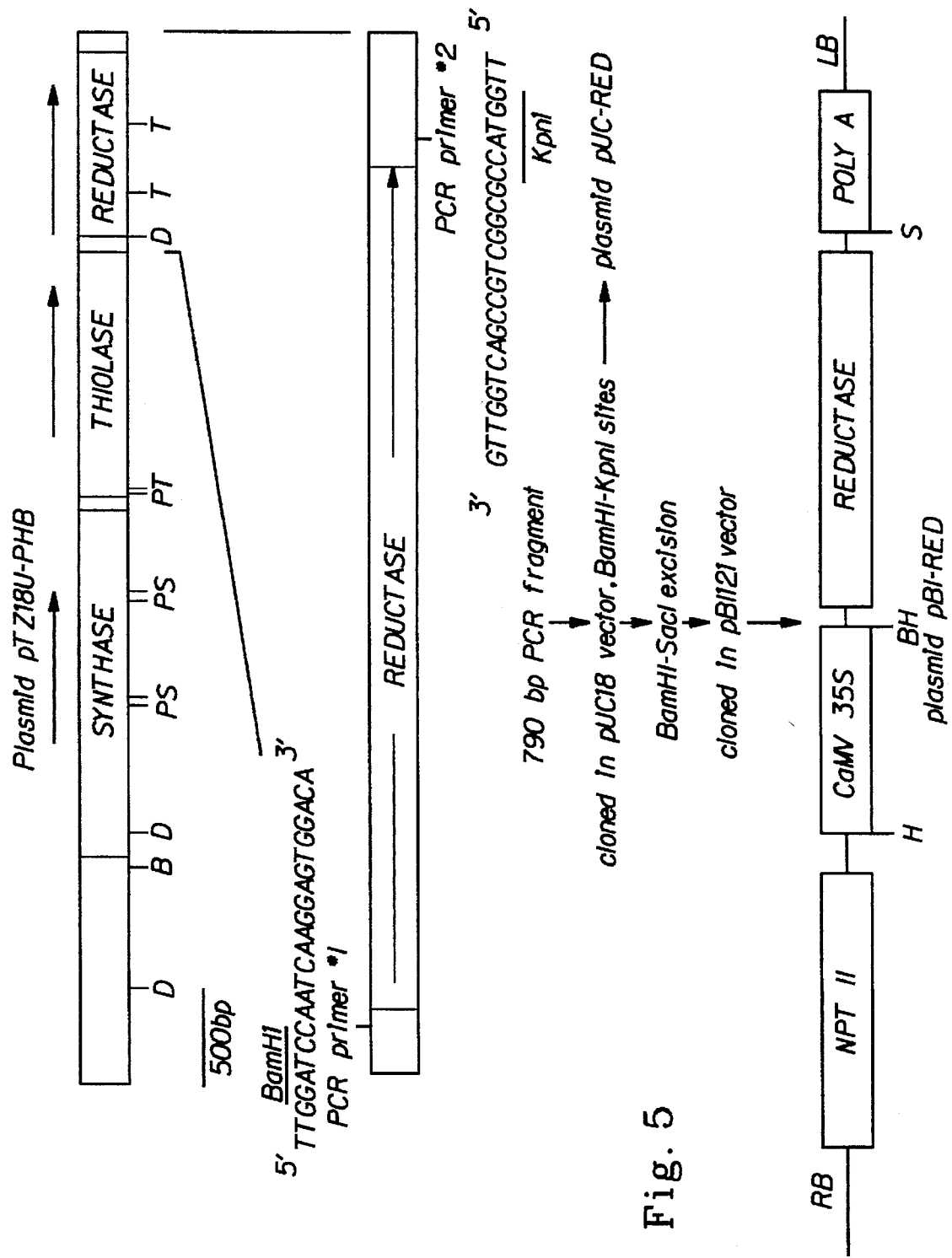
FIG. 5 shows a schematic summary of the steps involved in the construction of plasmids pUC-RED and pBI-RED. The purpose of this latter plasmid is to place the acetoactyl-CoA reductase gene from A. eutrophus under transcriptional control of the CaMV 35S promoter so that it will be expressed in higher plants. The top and bottom diagrams and abbreviations are described in FIG. 3. The middle diagram is an enlargement of the acetoacetyl-CoA reductase gene region. The location and sequence of the PCR primer #1 and #2 are indicated. The last nucleotide at the 3' end of PCR primer #1 corresponds to nucleotide 3952 in SEQ ID NO:1 and is the first nucleotide of the initiation codon for the reductase gene. The last nucleotide at the 3' end of PCR primer #2 is complementary to nucleotide 4708 in SEQ ID NO:1. The additional BamHI and KpnI restriction enzyme sites created by the PCR primers are indicated.
Figure 6:
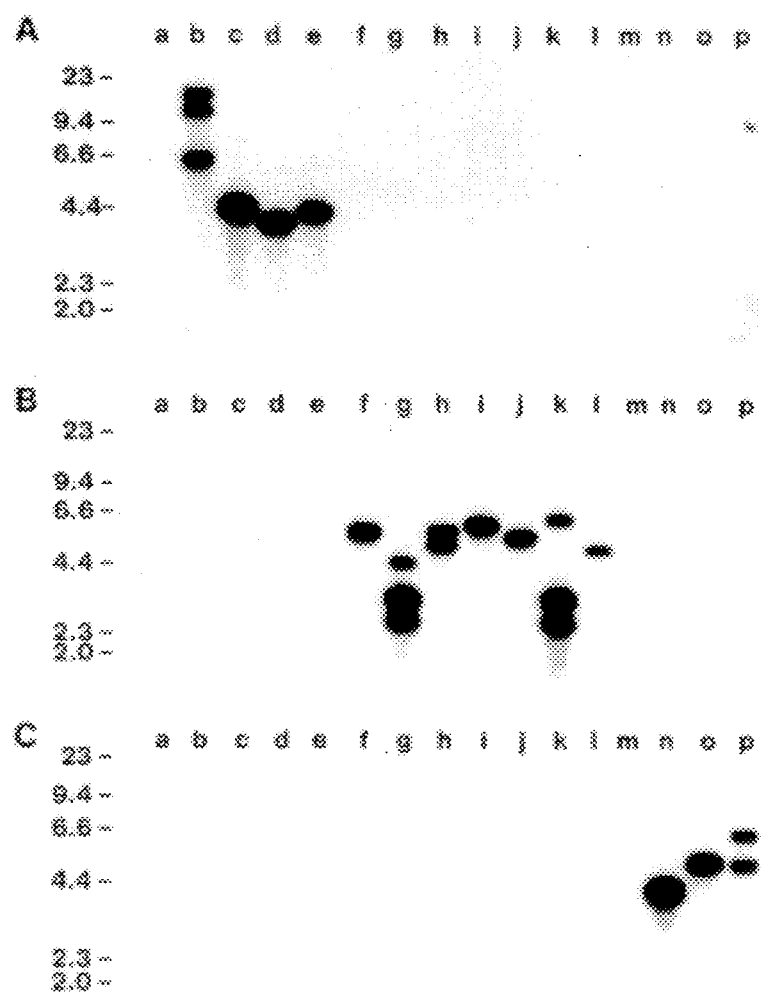
FIG. 6 shows Southern blot analysis of untransformed control and transgenic A. thaliana plants. One g of genomic DNA from untransformed A. thaliana race Rschew and from transgenic plants were digested with the restriction enzyme HindIII, the fragments were separated by agarose gel electrophoresis and transferred to nylon membranes. Filters were hybridized to $^{32}$P-labeled DNA fragments from genes (A) phbA, (B) phbB and (C) phbC. The genomic DNAs analyzed are: wild type A. thaliana race Rschew (lane a) and transgenics T4-3A (lane b), T3-2A (lane c), T4-2A (lane d), T4-3B (lane e) , RedB-2G (lane f), RedB-2B (lane g), RedB-2E (lane h), RedB-2C (lane i), RedD-3A (lane j), RedB-2A (lane k), RedB-2D (lane l), S12-3A (lane m), S8-1-2C (lane n), S8-1-2A (lane o) and S8PUC-2B (lane p). Numbers on the left side are length in kilobase pairs.

In order to verify the proper integration of the phb genes in the various trangenic plant lines produced, the genomic DNA of the trangenic plants was analyzed. High molecular weight DNA from control untransformed plants and from T3 transgenic plants transformed with the plasmids pBI-THIO, PBI-RED and pBI-SYN was isolated. The DNAs were digested with the restriction enzymes HindIII, the fragments separated by agarose gel electrophoresis and transferred onto a nylon filter. The restriction enzyme HindIII cuts only once at the 5'end of the CaMV 35S promoter in plasmids pBI-THIO, pBI-RED and pBI-SYN (FIGS. 3, 4 and 5). Fragments detected using phb gene specific probes should therefore represent junction fragments of the Ti vectors with the plant genomic DNA, or internal fragments of concatamerized Ti vectors. The inserts in plasmids pUC-THIO, pCU-RED and pUC-SYN were excised by treatment with EcoRI and HindIII, purified by agarose gel electrophoresis using DEAE cellulose membranes and labeled with $^{32}$P-deoxyribonucleotides by random priming. The labeled phb gene fragments were then used to probe the nylon filters. The filters were hybridized and subsequently washed under high stringency conditions. The result of these filter hybridizations is shown in FIG. 6. None of the three phb genes can be detected in untransformed control plants (FIGS. 6A, B and C, lane a). The phbA gene was detected in four of the transgenic lines produced by transformation with the plasmid pBI-THIO (FIGS. 6A, lanes b to e). The phbB gene was detected in seven of the transgenic plants produced by transformation with the plasmid pBI-RED (FIG. 6B, lanes f to l). Finally, the phbC gene was detected in three of the transgenic plants produced by transformation with the plasmid pBI-SYN (FIG. 6C, lanes m to p). Although the plant line S12-3A was resistant to 50 μg/ml of kanamycin, suggesting the integration of the NPTII gene, no phbC gene could be detected. It is likely that only the fragment of the Ti vector harboring the NPTII gene, and not the phbC gene, was integrated in the genomic DNA of plant line S12-3A.

Analysis of Expression of the phb Genes in Transgenic Plants

Figure 7:
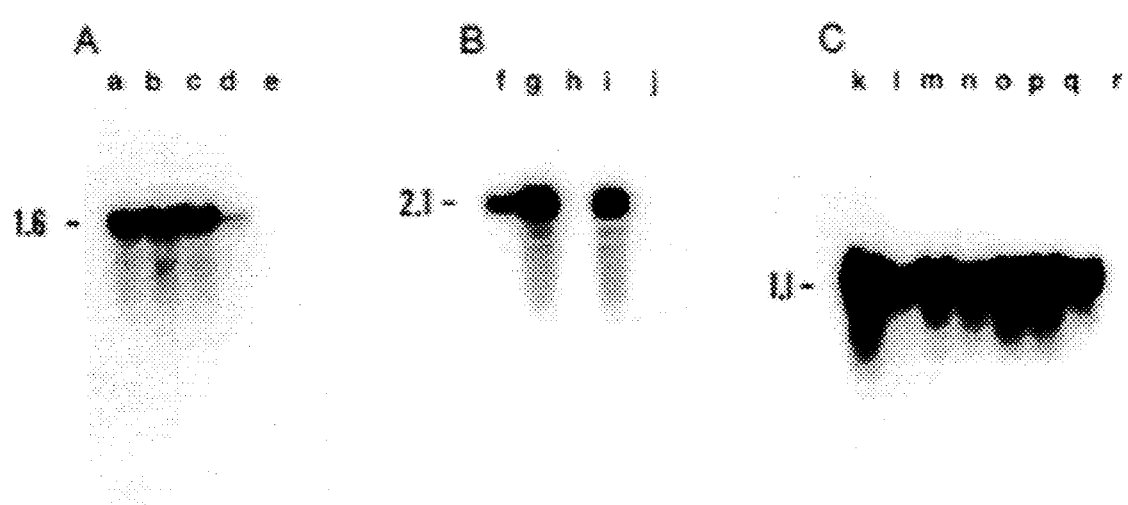
FIG. 7 shows Northern blot analysis of untransformed control and transgenic A. thaliana plants. Total RNA from wild type A. thaliana race Rschew (10 µg) and from transgenic plants (20 µg) were resolved by electrophoresis in formaldehyde-containing agarose gels and transferred to nylon membranes. Filters were hybridized to $^{32}$P-labeled DNA fragments from genes (A) phbA, (B) phbC and (C) phbB. The RNAs analyzed are from plants: T3-2A (lane a), T4-2A (lane b), T4-3B (lane c), T4-3A (lane d), wild type A. thaliana (lanes e, j and r), S8PUC-2B (lane f), S8-1-2C (lane g), S12-3A (lane h), 88-1-2A (lane i), RedB-2D (lane k), RedB-2E (lane l), RedB-2G (lane m), RedB-2A (lane n), RedB-2B (lane o), RedB-2C (lane p) and RedD-3A (lane q). Numbers are length in kilobase pairs.

In order to determine if the A. eutrophus phb genes were expressed in the various transgenic lines, the cloned genes present in plasmids pUC-THIO, pUC-RED and pUC-SYN were used as probes in filter hybridization experiments. Total RNA was extracted from untransformed control and T3 transgenic plants. The RNA was resolved by electrophoresis in formaldehyde-containing agarose gels and transferred to nylon filters by established procedures. The inserts of plasmids pUC-THIO, pUC-RED and pUC-SYN were excised by treatment with EcoRI and Hind III, purified by electrophoresis using DEAE cellulose membranes and labeled with $^{32}$P-deoxyribonucleotides by random priming. The labeled phb genes were used to probe the nylon filters. These experiments showed that none of the three phb probes hybridized to any RNA in the untransformed control plant (FIG. 7, lane e, j and r). By contrast, transgenic plants produced by transformation with pBI-THIO had RNA of 1.6 kbp which was complementary to the 3-ketothiolase gene (FIG. 7A, lanes a to d). The CaMV 35S promoter and poly-A addition sequences present on the pBI121-derived plasmids contribute approximately 300 bp to the final length of the mRNAs produced from the phb fusion genes. The level of 3-ketothiolase mRNA was low in plant line T4-3A relative to the other plant lines. Similarly, three of the transgenic lines produced by transformation with pBI-SYN had mRNA of 2.1 kbp corresponding to the PHB synthase gene (FIG. 7B, lanes f, g, and i). Transgenic line S12-3A had no detectable mRNA hybridizing to the phbC probe (FIG. 7B, lane h). This result is in accordance with the Southern blot analysis showing no integration of the phbC gene in the genomic DNA of line S12-3A (FIG. 6C, lane m). Finally, seven transgenic lines produced by transformation with the plamid pBI-RED had mRNA of 1.1 kbp which was complementary to the acetoacetyl-CoA reductase gene (FIG. 7C, lanes k to q). Thus, for each of the three phb genes, at least three independent transgenic plants were obtained which expressed complementary RNA of the expected size.

Although the presence of RNA indicates that the genes are transcribed, it does not provide any information that they are translated or that the translation product is functional. This was examined by assaying the transgenic plants for enzyme activity.

Transgenic plants produced by transformation with pBI-THIO were assayed for 3-ketothiolase activity by minor modifications of the assay described by Senior, P. J. and Dawes, E. A., Biochem. J. 134:225–238 (1973). Frozen leaf tissues from T3 plants were homogenized in Tris buffer and the clarified crude extracts were assayed for 3-ketothiolase activity. The results of these experiments are presented in Table 1. Extracts from untransformed A. thaliana plants had very low levels of 3-ketothiolase activity under the assay conditions. By contrast, each of the transgenic plants found to transcribe the phbA gene had substantially increased levels of thiolase activity. This indicated that the bacterial thiolase gene is functional when expressed in transgenic plants. However, the specific activity of 3-ketothiolase detected in the various transgenic plants was significantly lower compared to extracts prepared from E. coli harboring the phbA gene on the plasmid pTZ18U-PHB.

TABLE 1

| Levels of 3-ketothiolase activity in A. thaliana transgenic plants | |
|---|---|
| Sample | 3-Ketothiolase activity[a] |
| DH5alpha/PHB[b] | 9.5 |
| Wild type A. thaliana | 0.019 |
| T4-3A transgenic | 0.057 |
| T3-2A transgenic | 0.42 |
| T4-2A transgenic | 0.43 |
| T4-3B transgenic | 0.54 |

[a]Micromoles of acetoacetyl-CoA degraded per minute per milligram of protein. Values are an average of two to four measurements.
[b]E. coli DH5alpha containing the plasmid pTZ18U-PHB harboring the PHB operon.

Transgenic plants produced by transformation with plasmid pBI-RED were assayed for acetoacetyl-CoA reductase activity by minor modifications of the assay described by Senior, P. J. and Dawes, E. A., Biochem. J. 134:225–238 (1973). Leaves from T3 plants were homogenized in potassium phosphate buffer and the clarified extracts were assayed for acetoacetyl-CoA reductase activity. The results of these experiments are presented in Table 2. Extracts from untransformed A. thaliana plants had undetectable levels of acetoacetyl-CoA reductase activity under the assay conditions. By contrast, each of the transgenic plants found to transcribe the phbB gene had high levels of acetoacetyl-CoA reductase activity. This indicates that the bacterial acetoacetyl-CoA reductase gene is functional when expressed in transgenic plants. Furthermore, the specific activity of acetoacetyl-CoA reductase detected in six of the seven transgenic plants analyzed was significantly higher than in extracts from E. coli harboring the phbB genes on the plasmid pTZ18U-PHB.

TABLE 2

Levels of acetoacetyl-CoA reductase in A. thaliana transgenic plants

| Sample | Acetoacetyl-CoA reductase activity[a] |
| --- | --- |
| DH5alpha/PHB[b] | 1.4 |
| Wild type A. thaliana | <0.03 |
| RedB-2A transgenic | 12.5 |
| RedB-2B transgenic | 16.2 |
| RedB-2C transgenic | 9.1 |
| RedB-2D transgenic | 8.8 |
| RedB-2E transgenic | 1.6 |
| RedB-2G transgenic | 5.2 |
| RedD-3A transgenic | 2.3 |

[a]Micromoles of NADPH reduced per minute per milligram of protein. Values are an average of two to four measurements.
[b]E. coli DH5alpha containing the plasmid pTZ18U-PHB harboring the PHB operon.

Transgenic plants obtained by transformation with the plasmid pBI-SYN were not assayed for the presence of PHB synthase activity because of technical difficulties in measuring the activity of this enzyme in the absence of thiolase and reductase activities.

Production and Analysis of Hybrid Plants

Because higher plants contain an endogenous cytoplasmic 3-ketothiolase activity, the only additional enzymes required to produce PHB are acetoacetyl-CoA reductase and PHB synthase. These two genes were introduced into the same plant by cross-pollinating a transgenic line which was judged to be homozygous for the acetoacetyl-CoA reductase gene with a transgenic line which was judged to be homozygous for the PHB synthase gene. The hybrid seeds resulting from these crosses were grown in soil for two to three weeks before assaying for the presence of PHB.

In order to determine if the presence in plants of the acetoacetyl-CoA reductase and PHB synthase genes was sufficient for production and accumulation of PHB, extracts of chloroform-soluble material were made from control plants and hybrid plants containing both of these genes. The presence of PHB within these extracts was analyzed by gas chromatography (GC). Two methods were used to prepare plant extracts for GC analysis. These methods exploit both the highly polymerized nature of PHB ($10^6$ daltons on average for PHB produced from A. eutrophus) and its selective solubility in chlorinated hydrocarbons such as chloroform. Briefly, in method #1, whole leaves are placed in a 1:1 solution of chloroform and water and shaken by inversion for 16 hours at 65° C. Because molecules larger than approximately 50,000 daltons cannot pass through the plant cell wall, only low molecular weight water or chloroform-soluble products are extracted from the leaves under these conditions. The putative high molecular weight PHB is then extracted from the leaves by homogenizing the remaining tissue to disrupt the cell wall, and re-extracting it in a solution of 1:1 chloroform and water for 12 hours at 65° C. In method #2, whole leaf samples are successively extracted for 2 hours at 55° C. in 50% ethanol, 2 hours at 55° C. in 100% methanol and 15 minutes at 20° C. in 100% diethyl ether. The remaining tissue is then homogenized and extracted in chloroform at 100° C. for 4 hours. The products present in the final chloroform extract obtained from both of these methods were transesterified with ethanol and hydrochloric acid and analyzed by gas chromatography. The retention time of the transesterified plant products were compared to transesterified commercial PHB purified from A. eutrophus (Sigma Chemical Co., MO).

Figure 8:
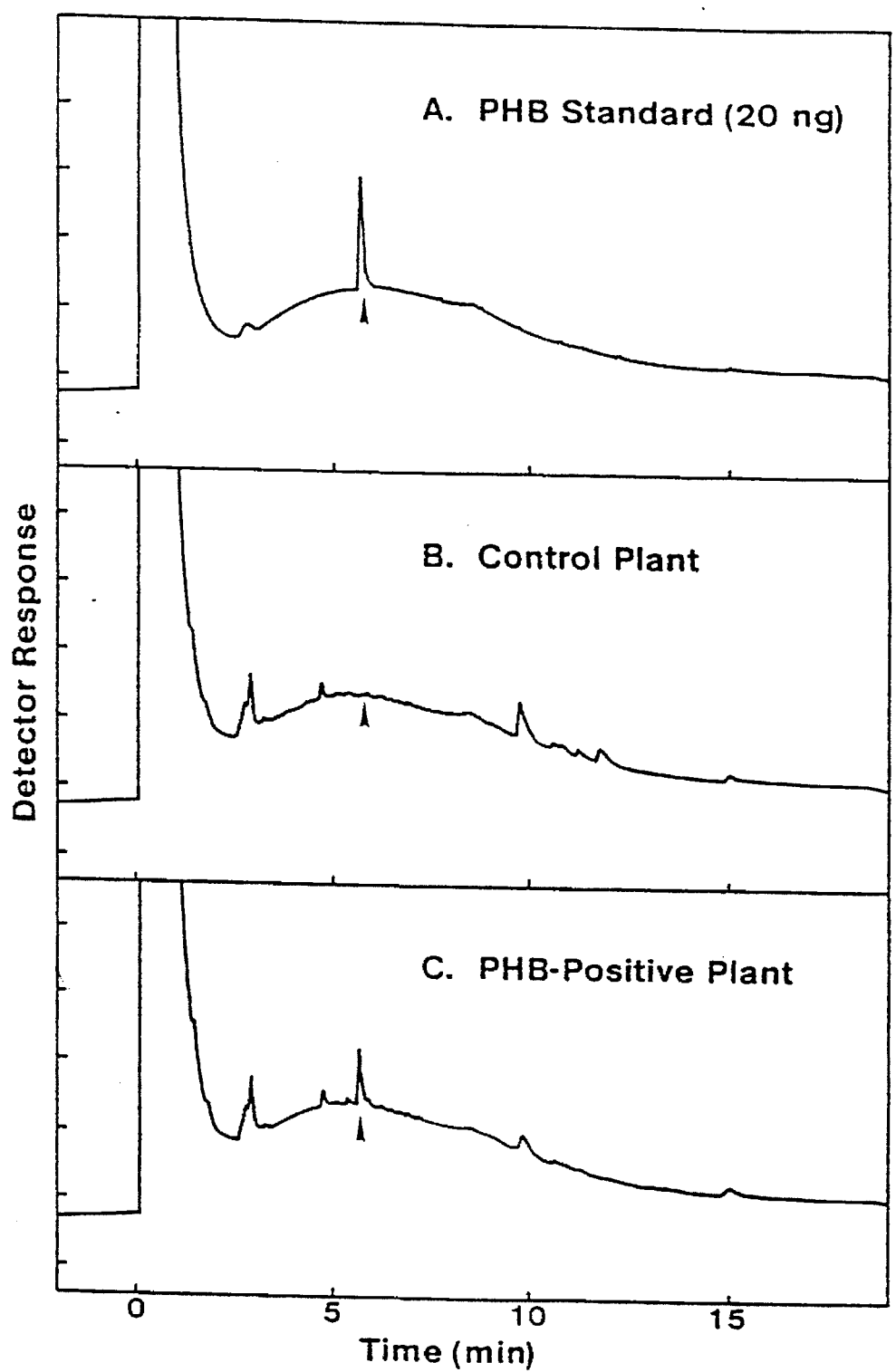
FIG. 8 shows gas chromatography (GC) of purified PHB and plant extracts. GC spectra of transesterified chloroform extracts of leaves from untransformed wild type A. thaliana race Rschew (B) and F1 hybrid between transgenic plants S8-1-2A and RedB-2C (C) were compared to the chromatogram of transesterified commercial PHB (A) . The arrows indicate the location of the ethyl-hydroxybutyrate peak.

Transgenic plants S8-1-2A and/or S8-1-2C were cross-pollinated with transgenic plants RedB-2A, -2C, -2D, -2G and RedD-3A. The resulting F1 seeds were sowed in soil and leaf samples or whole shoots of 2-3 week-old plants were collected and analyzed for the presence of PHB. An example of the results obtained using purification method #1 are shown in FIG. 8. A product present in the extracts of F1 plants having both the acetoacetyl-CoA reductase and the PHB synthase transgenes has a retention time identical to ethyl-hydroxybutyrate, as determined by comparison with the retention time of the transesterified product of commercial PHB. This new product, tentatively identified as ethyl-hydroxybutyrate, was only detected in F1 hybrid plants having both an active acetoacetyl-CoA reductase transgene and a PHB synthase transgene. A similar product could not be detected in transgenic plants having only one of the above mentioned genes or in untransformed A. thaliana plants. Furthermore, this product could not be detected in chloroform extracts of plant tissues which had not been previously homogenized. This indicates that the ethyl-hydroxybutyrate is derived from a high molecular weight precursor.

Figure 9:
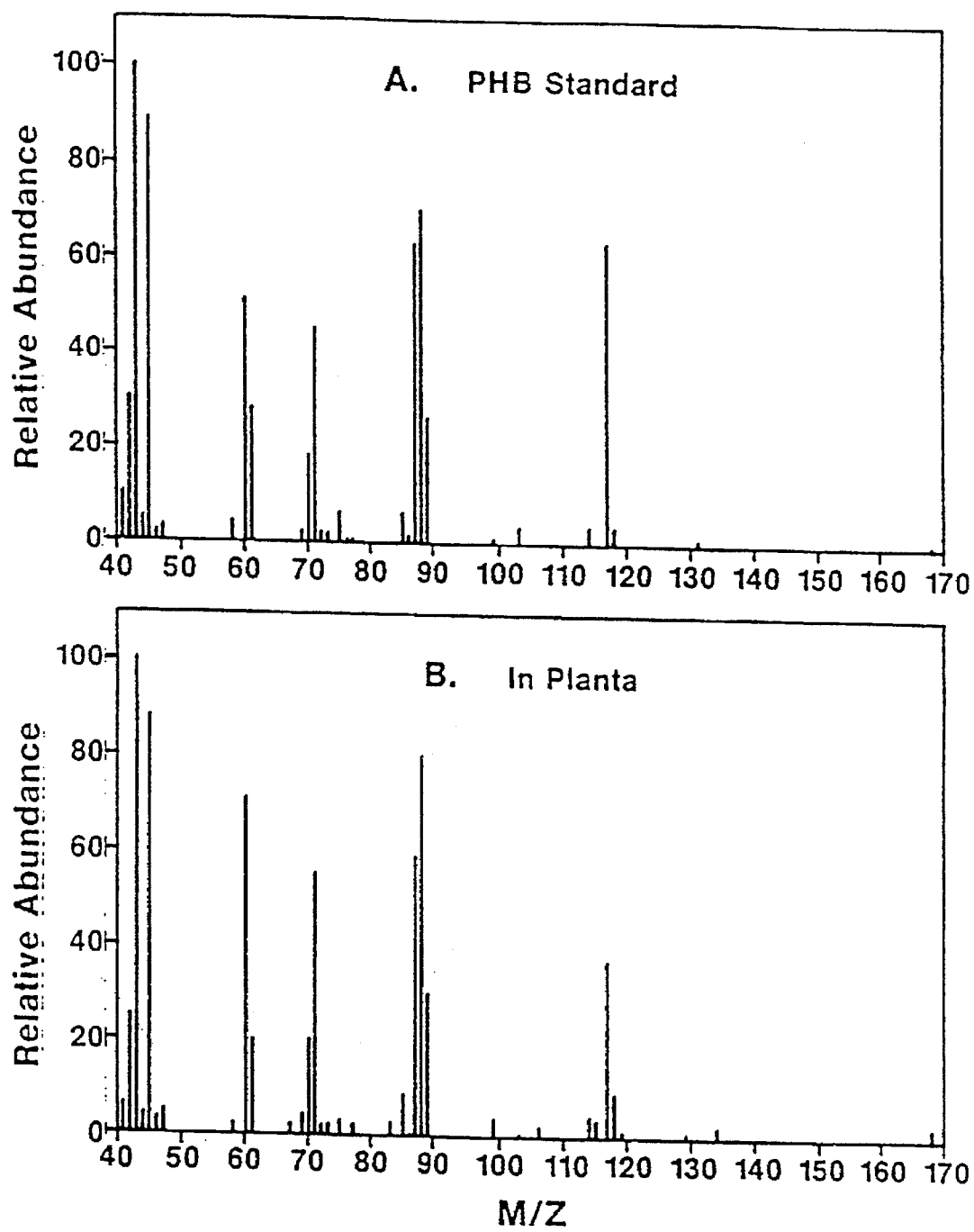
FIG. 9 shows gas chromatography-mass spectrometry analysis of ethyl-hydroxybutyrate prepared from a PHB standard and PHB from plant extracts. (A) Mass spectrum of transesterified commercial PHB; (B) the mass spectrum of the GC peak from leaf chloroform extract of F1 hybrid between S8-1-2A and RedB-2C having a retention time identical to ethyl-hydroxybutyrate (as shown in FIG. 8C).

The identity of the new plant product having a retention time identical to ethyl-hydroxybutyrate was analyzed by gas chromatography-mass spectrometry (GC-MS). GC-MS analysis was performed by the MSU-NIH Mass Spectrometry Facility. FIG. 9A shows the mass spectrometric spectra of ethyl-hdydroxybutyrate prepared from authentic PHB. FIG. 9B shows the mass spectrum of the putative ethyl-hydroxybutyrate extracted from an F1 hybrid plant which resulted from a cross between transgenic plants S8-1-2A and RedB-2C. The results indicated that the new plant product eluting with the same retention time as ethyl-hdyroxybutyrate also has the same fragmentation pattern as an authentic sample of ethyl-hyroxybutyrate. The fact that this new product can only be detected in extracts from leaf tissue which has previously been homogenized indicates that the ethyl-hydroxybutyrate is derived from material having a molecular weight greater than approximately 50,000 daltons (the approximate porosity of plant cell walls). Together, these data indicate that transgenic plants containing both the acetoacetyl-CoA reductase and the PHB synthase genes accumulate polyhydroxybutyrate. Table 3 shows a summary of the F1 plants that were analyzed by GC and GC-MS. Based on the GC analysis, the amount of PHB accumulated in leaves of F1 hybrids ranged from approximately 5 μg of PHB per gram of fresh weight of leaves for F1 hybrids between RedD-3A and S8-1-2C, to approximately 100 μg of PHB per gram fresh weight of leaves from F1 hybrid between RedB-2C and S8-1-2A.

TABLE 3

Summary of evidence for production of PHB in F1 hybrid plants

| Parental Transgenic Line[a] | Parental Transgenic Line[a] | |
|---|---|---|
| | S8-1-2C | S8-1-2A |
| RedD-3A | GC[b] | |
| | MS[c] | |
| RedB-2A | | TEM[d] (leaf) |
| | TEM (seed) | GC |
| RedB-2G | | TEM (leaf, seed) |
| | | GC |
| | | MS |
| RedB-2C | | TEM (leaf) |
| | | GC |
| | | MS |
| | TEM (leaf) | |
| RedB-2D | | |
| | | TEM (leaf) |

[a]Transgenic lines harboring the acetoacetyl-CoA reductase transgene were cross-pollinated with transgenic lines harboring the PHB synthase. The resulting F1 hybrids were analyzed for production of PHB.
[b]Evidence for production of PHB by gas chromatography analysis
[c]Evidence for production of PHB by gas chromatography-mass spectrometry.
[d]Detection of electron-lucent granules by transmission electron microscopy. In parenthesis is indicated the plant tissue analyzed.
[e]All blank spaces indicate that the analysis has not been performed.

Visual Inspection of PHB Granules in Hybrid Plants

Transmission electron microscopy (TEM) of bacteria accumulating PHB revealed electron-lucent granules of 0.2 to 0.5 µm in diameter surrounded by a membrane coat of about 2 nm thick (Lundgren, D. G., Pfister, R. M. and Merrick, J. M., J. Gert. Microbiol. 34:441–446 (1964)). To determine if similar granules could be detected in hybrid plants shown to be positive for PHB production by GC-MS analysis, plant tissues were examined by transmission electron microscopy. Transgenic plants S8-1-2A and/or S8-1-2C were cross-pollinated to transgenic RedB-2A, -2C, -2D, -2G and RedD-3A. The resulting F1 hybrid seeds and mature leaf material were fixed for analysis by transmission electron microscopy. Briefly, tissues were fixed in 3% glutaraldehyde and 1% osmium tetroxide and embedded in epoxy resin. Sections of 80–90 nm were stained with 5% uranyl acetate and lead citrate.

In one series of experiments, the F1 seeds were sowed in soil and leaves from 2-3 week-old plants were collected for TEM analysis. Inspection of the cells present in the leaves revealed the presence of agglomerations of electron-lucent granules. These granules were detected in all analyzed F1 hybrid plants resulting from crosses between transgenics having the PHB synthase gene and transgenics having the acetoacetyl-CoA reductase gene. Examples are shown in FIGS. 10A through 10F. Similar granules were never detected in the parental transgenic lines having only the PHB synthase or the acetoacetyl-CoA reductase genes, nor was it detected in untransformed A. thaliana. In F1 hybrid leaf tissues, the granules were detected in mesophyll cells (FIGS. 10A to 10E). The agglomerate of electron-lucent granules were detected most frequently in the nucleus (FIGS. 10A to 10C), but similar structures were also detected in the cytoplasm (FIG. 10E) and the vacuole (FIG. 10D) of the F1 hybrid leaf tissues. In the nucleus and cytoplasm, individual granules could reach a maximum size of approximately 0.18 µm. In the vacuoles, the granules were generally larger, reaching a maximum diameter of approximately 0.55 µm. At higher magnification, the nuclear granules appear to be surrounded by electron-dense material. Both the size and apparent structure of these granules are very similar to granules observed in bacteria which accumulate PHB.

Figure 10A:
FIGS. 10A–10F show transmission electron micrographs (TEM) of leaf and seed of PHB-positive transgenic A. thaliana plants. Transgenic plants S8-1-2A and S8-1-2C were cross-pollinated with transgenic plants RedB-2D or RedB-2A. The resulting F1 seeds were sowed in soil and leaf samples from 2–3 week-old plants were analyzed by TEM (FIGS. 10A to 10E). Some F1 seeds were also soaked in water for 24 hours, the embryo dissected out of the seed coat and the cotyledons analyzed by TEM (FIG. 10F). Two adjacent leaf mesophyll cells from RedB-2D X S8-1-2A F1 hybrid showing agglomerations of electron-lucent granules in the nucleus as shown in FIG. 10A.
Figure 10B:
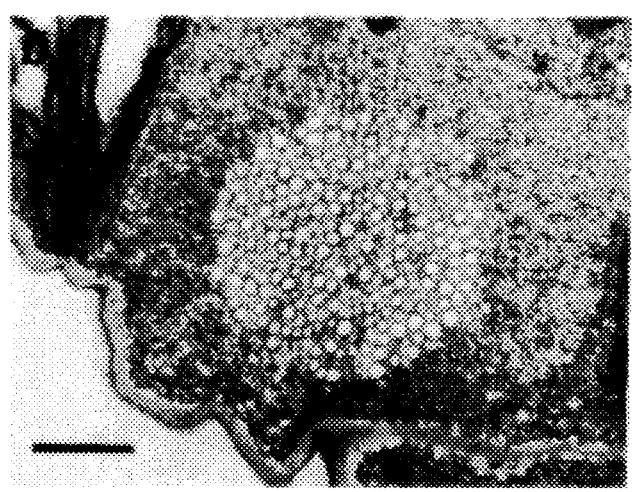
Figure 10C:
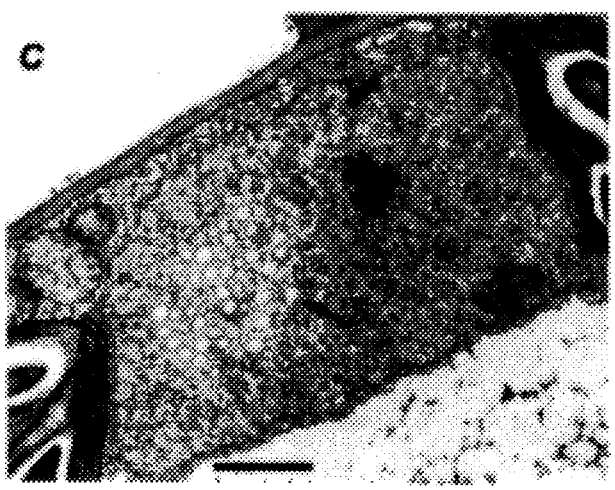
Figure 10D:
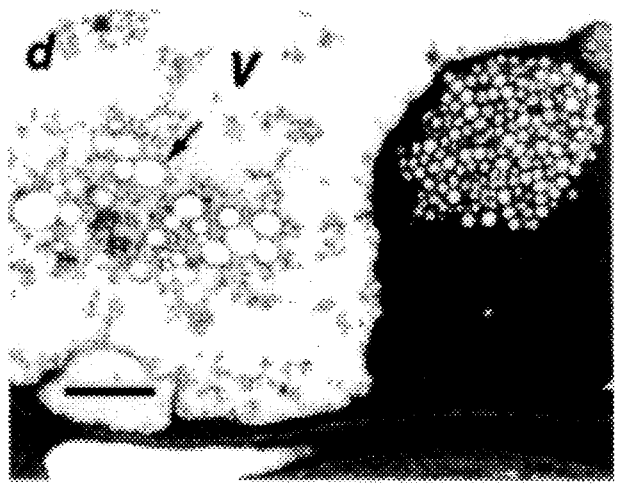
Figure 10E:
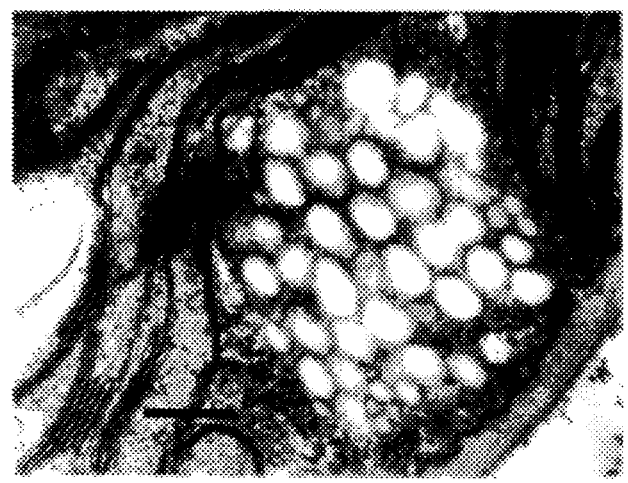
Figure 10F:
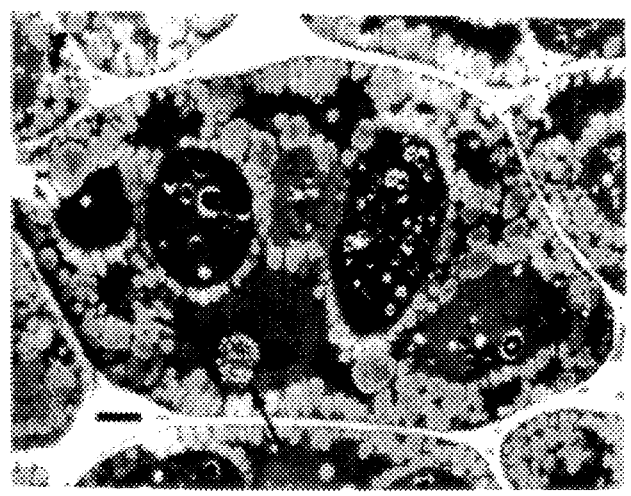

In a second series of experiments, F1 seeds were soaked in water for 24 hours, the embryos were dissected out of the seed coat and tissues were fixed. Analysis of the embryonic cotyledons revealed the presence of agglomeration of electron-lucent granules in the nucleus (FIG. 10F). The granules could reach a maximum diameter of 0.18 µm. These granules could only be detected in the nucleus of F1 hybrid embryos resulting from crosses between transgenics having the PHB synthase gene and transgenics having the acetoacetyl-CoA reductase gene. No granules could be detected in either of the parental transgenic plants having only one of the ectopic genes, or in untransformed wild type A. thaliana. Table 3 shows a summary of the F1 plants that were analyzed by TEM.

The data described above show a positive correlation between detection of PHB by GC-MS and the presence of granules at the electron microscope level. The size, shape and presence of electron-dense material surrounding the individual granules very closely resembles the granules present in bacteria producing PHB. Finally, both the detection of PHB by GC-MS and the presence of electron-lucent granules are only observed in hybrid plants possessing both the acetoacetyl-CoA reductase and the PHB synthase transgenes. Together, these data indicate that the granules observed in F1 hybrid plants are composed of polyhydroxybutyrate.

DISCUSSION

In these studies, it has been demonstrated that bacterial genes encoding enzymes required for PHB synthesis can be stably introduced into a higher plant in such a way that the genes are transcribed and produce transcripts of the expected size. It was further shown that, in the case of the phbA and phbB genes, the presence of these genes in transgenic plants confers an increase in the level of 3-ketothiolase or acetoacetyl-CoA reductase enzyme activity, respectively. Thus, it is clear that these two gene products are functional when translated in the plant. Because of technical difficulties associated with assaying PHB synthase activity directly, the amount of PHB synthase activity in the transgenic plants was not determined.

It was shown that only plant extracts from F1 transgenic plants expressing both the acetoacetyl-CoA reductase and PHB synthase produce a new high molecular weight chloroform-soluble compound, which upon transesterification with ethanol and hydrochloric acid, produces ethylhydroxybutyrate. These data indicate that the new compound is polyhydroxybutyrate. In addition, these data are an indirect evidence for the production of a functional PHB synthase in transgenic plants. This is important since an in vitro assay for the PHB synthase activity could not be performed. Furthermore, production of PHB also indirectly indicate that D(−)-hyroxybutyryl-CoA, the substrate for the PHB synthase, is produced in plants. This hydroxyacyl-CoA is not naturally found in plants.

Transmission electron microscopy further substantiates the claim that PHB is produced in transgenic plants. Analysis of embryonic cotyledons and mature leaves of F1 transgenic plants expressing both the acetoacetyl-CoA reductase and the PHB synthase revealed agglomerates of electron-lucent granules having a size and structure very similar to granules found in bacteria producing PHB, such as A. eutrophus. These granules were found most frequently in the nucleus, but were also detected in the vacuole and the cytoplasm of F1 hybrid plants.

In the experiments described in this work, the products of the phbA, phbB, and phbC genes from A. eutrophus are most likely expressed in the cytoplasm, since no specific amino acid sequences were added to the proteins to target them specifically into any organelles. Since the cytoplasm of plant cells already contains a 3-ketothiolase, only the additional expression of the acetoactyl-CoA reductase and PHB synthase was required to produce PHB. The fact that granules are found in the nucleus and vacuoles is not necessarily contradictory with the expression of the enzymes in the cytoplasm. Since nuclear membranes dissemble and reassemble during cell division, PHB granules initially produced in the cytoplasm could be entrapped within the newly reforming membranes of the nucleus. Alternatively, because of their hydrophobicity, PHB granules could pass through the membranes of the nucleus or vacuole.

In an alternative approach, PHB production could be localized to a specific plant cell organelle through targeted expression of the enzymes involved in PHB synthesis to the organelle. In this case, if the targeted organelle does not express an active 3-ketothiolase, expression of an exogenous 3-ketothiolase activity would be required, in addition to the acetoacetyl-CoA reductase and the PHB synthase, for the production of PHB.

The long term goal of PHB or PHA production in higher plants is to divert carbon away from major storage compounds such as lipid, starch or terpenoids, to channel it towards PHA synthesis. This goal will require tissue-specific expression as well as potentially organelle-specific expression of the enzymes involved in PHA synthesis.

Oil producing crops are likely targets for genetic engineering. Lipids are synthesized in the plastid using acetyl-CoA, the same precursor used in synthesis of PHB and other PHA. Therefore, genetic engineering of oil crops will require targeting the PHA biosynthetic enzymes into the plastid. Examples of oil crops that could be engineered for PHA production are rapeseed, sunflower and oil palm. Rapeseed and sunflower are major crops in North America and can be transformed with foreign DNA. Alternatively, PHA production could be targeted into the mesocarp of the oil palm fruit. Because lipids produced in the mesocarp are not essential for the survival of the tree or the embryo, the production of PHA should have no deleterious effects on palm trees. Unfortunately, no transformation techniques are yet available for oil palm.

PHA production could also be targeted to the roots and tubers of sugar beets and potatoes, crops which accumulate large amounts of starch. The major problem with this approach is that since starch and PHA do not use the same precursors, potentially multiple modifications in carbon metabolism will be required before carbon could be diverted away from starch into PHA.

Possibly the most direct approach to PHA production would be to use crops accumulating large amounts of terpenoids, such as carrot which accumulates carotenoids, or the mexican yam which accumulates sterols. Since terpenoids use the same precursors as PHA (acetyl-CoA and acetoacetyl-CoA), diverting carbon into PHA production could be more easily achieved.

MATERIALS AND METHODS

Construction of DNA Recombinants

*E. coli* strain DH5alpha harboring plasmids were grown in LB broth supplemented with kanamycin (50 µg/ml) or ampicillin (50 µg/ml). Large-scale preparations of plasmid DNA was done by the alkaline lysis and polyethylene glycol precipitation procedure as described by Sambrook, J., Fritsch E. F. and Maniatis, T., Molecular Cloning, a laboratory manual, Cold Spring Harbor Laboratory Press (1989). Plasmid DNA was cleaved with restriction endonucleases according to the manufacturer's recommendations (New England Biolabs, Mass; Promega Corp., WI; Boehringer Mannheim Biochemicals, IN; Stratagene, CA), separated by agarose gel electrophoresis and visualized by ethidium bromide staining as described by Sambrook, J., Fritsch, E. F. and Maniatis, T., Molecular cloning, a laboratory manual, Cold Spring Harbor Laboratory Press (1989). The DNA fragments were recovered from the agarose gel with DEAE membranes (NA-45 DEAE membrane, Schleicher and Schuell, Inc., NH). Briefly, DNA is electrophoresed onto a strip of NA-45 and the membrane is washed in 0.15M NaCl, 0.1 mM EDTA and 20 mM Tris-HCl (pH 8). The DNA is then eluted in 1.0M NaCl, 0.1 mM EDTA and 20 mM Tris-HCl (pH 8) at 65° C. for 1 to 2 hours. The DNA is further purified by phenol-chloroform extraction and ethanol precipitation. In some experiments, the recessed 3' termini of DNA fragments were converted into blunt ends with T4 DNA polymerase using the protocol described in Sambrook, J., Fritsch, E. F. and Maniatis, T., Molecular cloning, a laboratory manual, Cold Spring Harbor Laboratory Press (1989). Ligation of DNA fragments with cohesive or blunt ends was done at 14° C. for 16 hours in buffer containing 50 mM Tris-HCl (pH 7.6), 5 mM $MgCl_2$, 5% (w/v) polyethylene glycol 8000, 0.5 mM ATP and 5 mM dithiothreitol as described by Sambrook, J., Fritsch, E. F. and Maniatis, T., Molecular cloning, a laboratory manual, Cold Spring Harbor Laboratory Press (1989). A fraction of the ligation reaction was transferred into *E. coli* by the rubidum chloride method as described by Hanahan, D., J. Mol. Biol. 166:557–580 (1983). The transformed bacteria were plated on agar plates containing LB broth and either 50 µg/ml kanamycin or 50 µg/ml ampicillin. Bacterial colonies containing recombinant plasmids were identified by hybridization with $^{32}$P-labeled DNA probes as described by Sambrook, J., Fritsch, E. F. and Maniatis, T., Molecular cloning, a laboratory manual, Cold Spring Harbor Laboratory Press (1989), except that nylon membranes (Hybond-N, Amersham, IL) were used instead of nitrocellulose membranes. Preparation of radiolabeled DNA probes and hybridization are described in a following section. Small-scale preparation of plasmid DNA was done by the alkaline lysis method as described by Sambrook, J., Fritsch, E. F. and Maniatis, T., Molecular cloning, a laboratory manual, Cold Spring Harbor Laboratory Press (1989).

Oligonucleotides were synthesized on an Applied Biosystems 380A DNA synthesizer according to the manufacturer's instructions (Applied Biosystems, CA). The oligonucleotides with a dimethoxytrityl group attached to the 5' ends were purified on a Varian 5000 HPLC equipped with a C18 column (Varian Instrument Group, TX). The oligonucleotides were resuspended in 0.1M triethylamine and injected onto a C18 column preequilibrated with 12% acetonitrile/ 88% 0.1M triethylamine-acetate (pH7) (solvent A). The HPLC program was set as follows: flow rate, 0.9 ml/min; maximum pressure, 200 psi; time 0 min, 88% solvent A/12% solvent B (acetonitrile); time 3 min, 88% solvent A/12% solvent B; time 21 min, 65% solvent A/35% solvent B; time 25 min, 65% solvent A/35% solvent B. The purified oligonucleotides were detritylated in 80% acetic acid for 10 min and dried under nitrogen. The oligonucleotides were dissolved in 10 mM Tris-HCl (pH 7.5) and 0.1 mM EDTA, extracted three times with equal volumes of ethyl acetate and precipitated with ethanol.

Polymerase chain reaction (PCR) was performed using a Perkin-Elmer Cetus DNA thermal cycler (Perkin-Elmer, CT). The reaction mixture contained 100 pmoles of oligonucleotides, PCR primer #1 and #2 (see FIG. 5), 200 ng of plasmid pTZ18U-PHB linearized with the restriction enzyme EcoRI, 125 μM dNTP, 50 mM KCl, 10 mM Tris-HCl (pH 8.3), 2.5 mM $MgCl_2$, 0.01% gelatin and 2.5 units of Taq polymerase (Perkin-Elmer, CT). The DNA thermal cycler program was as follows: 3 min at 94° C., 40 cycles of the sequence 1 min at 94° C.—3 min at 55° C.—3 min at 72° C., and finally 7 min at 72° C. The PCR product was isolated by agarose gel electrophoresis and elution with DEAE cellulose membrane.

Production of Transgenic Plants

The Ti plasmid vectors used to produce transgenic plants were first transferred into *Agrobacterium tumefaciens* strain C58-pGV3850 by electroporation (Zabrisky, P. et al., EMBO 2:2143–2150 (1983); and Sambrook, J., Fritsch, E. F. and Maniatis, T., Molecular cloning, a laboratory manual, Cold Spring Harbor Laboratory Press (1989)). *Arabidopsis thaliana* race Rschew were grown aseptically on vertical petri plates containing mineral elements, 0.8% agar (Difco) and 1% sucrose as described by Estelle, M. A. and Somerville, C., Mol. Gen. Genet. 206:200–206 (1987) and Schiefelbein, J. W. and Somerville, C. R., Plant Cell 2:235–243 (1990). Roots from 10 to 12 day-old plants were excised and used for transformation as described by Valvekens, D., Van Montagu, M. and Van Lijsebettens, M., Proc. Natl. Acad. Sci USA 85:5536–5540 (1988).

Seeds from T0 and T1 transgenics plants were grown on media containing mineral elements, 1% sucrose, 0.8% agar (Difco) and 50 μg/ml kanamycin. After 10 to 14 days of growth, kanamycin resistant ($Km^r$) transgenic plants had green leaves while untransformed kanamycin sensitive ($Km^s$) plants had yellow leaves. At this stage, $Km^r$ plants could be removed from the agar plates and transplanted into fertilized soil.

Extraction and Restriction Endonuclease Cleavage of Genomic DNA

Wild type and transgenic plants were grown in soil for 2 to 3 weeks and approximately 5 g of leaf material was collected and frozen in liquid nitrogen. High molecular weight DNA was extracted from the frozen plant tissues as described by Rogers, S. C. and Bendich, A. J., Plant Molecular Biology Manual A6:1–10 (1988). Restriction endonuclease cleavage with the enzyme HindIII was performed under the conditions recommended by the manufacturer (New England Biolabs Inc., Mass).

Agarose Gel Electrophoresis and Hybridization Procedure

DNA analysis by agarose gel electrophoresis and transfer to nylon membranes (Hybond-N, Amersham, Il) were done using established procedures described by Southern, E. M., J. Mol. Biol. 38:503–517 (1975) and Sambrook, J., Fritsch, E. F. and Maniatis, T., Molecular cloning, a laboratory manual, Cold Spring Harbor Laboratory Press (1989). Specific cloned DNA fragments to be used as probes were excised from the vector with appropriate restriction endonucleases, the inserts were purified from the vector by agarose gel electrophoresis and electroelution using DEAE cellulose membranes. Probes were labeled with $^{32}P$-deoxyribonucleotides by the random primer extension method using hexamers as described by Feinberg, A. P. and Volgelstein, B., Anal. Biochem. 136:6–13 (1983). Nylon filters were hybridized with labeled probes and exposed on film as described by Poirier, Y. and Jolicoeur, P., J. Virol. 63:2088–2098 (1989).

RNA Isolation and Electrophoresis

Total RNA was isolated from frozen leaf samples as described by Puissant, C. and Houdebine, L. M., BioTechniques 8:148–149 (1990). The isolated RNA was separated by electrophoresis in agarose gel containing formaldehyde and transferred onto nylon membranes (Hybond-N, Amersham, Il) as described by Sambrook, J., Fritsch, E. F. and Maniatis, T., Molecular cloning, a laboratory manual, Cold Spring Harbor Laboratory Press (1989). The nylon filters were hybridized with labeled probes as described in the previous section.

Assay for 3-Ketothiolase Activity

One gram of frozen leaf samples were homogenized in 2 ml of ice-cold buffer containing 100 mM Tris-HCl (pH 8.0), 40 mM $MgCl_2$ and 5 mM beta-mercaptoethanol. The homogenate was clarified by centrifugation at 10000×g for 2 min and the supernatant transferred to a fresh tube. The protein content of the extract was measured by the Bradford assay using the BioRad protein assay kit (BioRad Laboratories, CA). Between 3 to 30 μg of plant protein extracts were used per assay. Protein extracts were also prepared from bacteria. In this case, stationary cultures of bacteria were pelleted by centrifugation, washed once with ice-cold assay buffer and resuspended in 200 μl of the same buffer. The bacterial suspension was lysed by sonication, the homogenate clarified by centrifugation and the protein content of the extract determined by the Bradford assay. Between 0.2 to 1 μg of bacterial protein extract was used per assay. Activity of the 3-ketothiolase enzyme in the different extracts was assayed according to the procedure of Senior, P. J. and Dawes, E. A., Biochem. J. 134:225–238 (1973).

Assay for Acetoacetyl-CoA Reductase Activity

One gram of frozen leaf samples were homogenized in 2 ml of ice-cold buffer containing 100 mM $KH_2PO_4$ (oH 5.5), 0.02 mM $MgCl_2$ and 4.0 mM beta-mercaptoethanol. The homogenate was clarified by centrifugation at 10000×g for 2 min and the supernatant transferred to a fresh tube. The protein content of the extract was measured by the Bradford assay using the BioRad protein assay kit. Between 0.8 to 10 μg of plant protein extract was used per assay. Bacterial extracts were also prepared in the assay buffer essentially as described in the previous section. Activity of the acetoacetyl-CoA reductase enzyme was assayed according to the procedure of Senior, P. J. and Dawes, E. A., Biochem. J. 134:225–238 (1973).

Gas Chromatography and Mass Spectroscopy Analysis

Two methods were used to prepare plant extracts for GC analysis. In method #1, between 0.005 and 0.05 g of fresh or frozen plant material (leaves or whole shoots) was extracted in 1 to 2 ml of a 1:1 solution of chloroform and water at 65° C. for 16 hours with constant agitation. The plant material was then homogenized in water and re-extracted in a 1:1 solution of chloroform and water for 16 hours at 65° C. with constant agitation. The chloroform phase was transferred to a new tube and extracted once with an equal volume of water. The final volume of the chloroform phase was adjusted to 0.5 ml and used for transesterification with ethanol and HCl as described below. In method #2, between 0.005 to 0.15 g of frozen or fresh plant material was successively extracted in 50% ethanol at 55° C. for 2 hours, 100% methanol at 55° C. for 2 hours and 100% diethylether for 15 minutes at room temperature. The remaining tissue was then homogenized in water, dried and extracted in 0.5 ml of chloroform for 4 hours at 100° C.

The final chloroform extracts (0.5 ml) obtained by method #1 and #2 was transesterified by adding 0.2 ml of concentrated HCl and 1.7 ml of 100% ethanol and heating at 100° C. for 2 hours. The reaction mixture was then cooled down to room temperature, the chloroform phase extracted twice with 2 ml of 0.9% NaCl (w/v) and the final organic phase reduced to 100 μl. As a standard, commercial PHB (Sigma Chemical Co., MO) was dissolved in warm chloroform and 1 mg was transesterified as described above.

The chloroform phase containing the ethyl esters were transferred to a GC vial for injection of 1 μl into a Hewlett Packard 5890 series II GC equipped with a programmable autosampler and a SP-2330 glass capillary column (Supelco, PA). The approximate linear velocity was 20 cm/s with helium as the carrier gas. The temperature of the injection port was set at 220° C., and that of the flame ionization detector port was set at 220° C. The following temperature profile was used: 4 minutes at 65° C., followed by a temperature increase rate of 20° C./minute up to 195° C., 3.5 minutes at 195° C., a post-run temperature decrease rate of 20° C./minute down to 65° C.

The identity of peaks of interest was established by GC-mass spectrometry. Electron impact mass spectral data was obtained on a JEOL JMS-AX505H mass spectrometer coupled with a Hewlett Packard 5890 GC. The following parameters were used: source temperature, 200° C.; ionization current, 100 μA; accelerating voltage, 3 keV. A J & W Scientific Co. column DB-225 was directly inserted into the mass spectrometer source and helium was used as carrier. The splitless injector was held at 260° C. and the transfer line at 260° C. The same GC oven temperature profile was used (see previous paragraph).

Transmission Electron Microscopy

Plant tissues were fixed with 3% glutaraldehyde in 0.1M phosphate buffer (pH 7.2) for 1.5–2 hours at room temperature. The samples were washed 4 times in 0.1M phosphate buffer (pH 7.2) and fixed in 1% $OsO_4$ in phosphate buffer for 2 hours at room temperature. The tissues were then dehydrated in a graded ethanol series and embedded in Spurrs epoxy resin. Sections of 80–90 nm were cut, placed on a copper grid and stained in 5% uranyl acetate for 30 to 45 minutes, followed by staining in Reynolds lead citrate for 3 to 4 minutes. Sections were viewed in a JEOL 100CXII transmission electron microscope operated at 80 kV.

Other Plants

Although the specific example of the invention described here involved the plant *Arabidopsis thaliana* and genes from *Alcaligenes eutrophus*, the invention is of general utility. The claims pertaining to production of polyhydroxybutyrate and/or polyhydroxyalkanoate in plants is not limited to *Arabidopsis thaliana*, or linked specifically to the use of genes from *Alcaligenes eutrophus*. The claims described below describe a general method for the production of polyhydroxyalkanoate in plants through the introduction of foreign DNA material into plant cells. Such plants include the plants discussed previously and carrot, sunflower, tobacco, tomato and potato, for instance.

The seeds from the various lines of plants have been deposited under the Budapest Treaty with the American Type Culture Collection, 12301 Parklawn Drive, Rockville, MD 20852. These lines include RedD-3A (ATCC 75044) containing the acetoacetyl-CoA reductase gene; S8-1-2A (ATCC 75043) containing the PHB synthase gene and T4-2A (ATCC 75042) containing the 3-ketothiolase gene. The genes are each shown in Sequence ID NO:1.

The foregoing specific description is only illustrative of the present invention and it is intended that the present invention be limited only by the hereinafter appended claims.

---

We claim:

1. A transgenic plant material comprising foreign DNA encoding an enzyme having catalytic activity of 3-ketothiolase.

2. The transgenic plant material of claim 1, wherein the foreign DNA encodes an enzyme having catalytic activity of an enzyme encoded by positions 2696-3877 of SEQ ID NO:1.

3. The transgenic plant material of claim 2, wherein the foreign DNA encodes an enzyme encoded by positions 2696-3877 of SEQ ID NO:1.

4. The transgenic plant material of claim 3, wherein the has the DNA sequence of positions 2696-3877 of SEQ ID NO:1.

5. A transgenic plant material comprising foreign DNA encoding an enzyme having catalytic activity of acetoacetyl-CoA reductase.

6. The transgenic plant material of claim 5, wherein the foreign DNA encodes an enzyme having catalytic activity of an enzyme encoded by positions 3952-4692 of SEQ ID NO:1.

7. The transgenic plant material of claim 6, wherein the foreign DNA encodes an enzyme encoded by positions 3952-4692 of SEQ ID NO:1.

8. The transgenic plant material of claim 7, wherein the foreign DNA has the DNA sequence of positions 3952-4692 of SEQ ID NO:1.

9. A transgenic plant material comprising foreign DNA encoding an enzyme having catalytic activity of polyhydroxyalkanoate synthase.

10. The transgenic plant material of claim 9, wherein the foreign DNA encodes an enzyme having catalytic activity of an enzyme encoded by positions 842-2611 of SEQ ID NO:1.

11. The transgenic plant material of claim 10, wherein the foreign DNA encodes an enzyme encoded by positions 842-2611 of SEQ ID NO:1.

12. The transgenic plant material of claim 11, wherein the foreign DNA has the DNA sequence of positions 842-2611 of SEQ ID NO:1.

13. A transgenic plant material comprising:
 a) a first DNA sequence encoding an enzyme having catalytic activity of ketothiolase;
 b) a second DNA sequence encoding an enzyme having catalytic activity of acetoacetyl-CoA reductase; and
 c) a third DNA sequence encoding an enzyme having catalytic activity of polyhydroxyalkanoate synthase;
wherein at least the second DNA sequence and third DNA sequence are ectopic; and wherein expression of the DNA sequences leads to the production in the plant material of one or more granules comprising polyhydroxybutyrate.

14. The transgenic plant material of claim 13, wherein
 a) the first DNA sequence encodes an enzyme having the catalytic activity of an enzyme encoded by positions 2696-3877 of SEQ ID NO:1;
 b) the second DNA sequence encodes an enzyme having the catalytic activity of an enzyme encoded by positions 3952-4692 of SEQ ID NO:1; and
 c) the third DNA sequence encodes an enzyme having the catalytic activity of an enzyme encoded by positions 842-2611 of SEQ ID NO:1.

15. The transgenic plant material of claim 14, wherein
 a) the first DNA sequence encodes an enzyme encoded by positions 2696-3877 of SEQ ID NO:1;
 b) the second DNA sequence encodes an enzyme encoded by positions 3952-4692 of SEQ ID NO:1; and
 c) the third DNA sequence encodes an enzyme encoded by positions 842-2611 of SEQ ID NO:1.

16. The transgenic plant material of claim 15, wherein
 a) the first DNA sequence has the DNA sequence of positions 2696-3877 of SEQ ID NO:1;
 b) the second DNA sequence has the DNA sequence of positions 3952-4692 of SEQ ID NO:1; and
 c) the third DNA sequence has the DNA sequence of positions 842-2611 of SEQ ID NO:1.

17. The transgenic plant material of claim 13 as a seed or propagule of the seed.

18. The transgenic plant material of claim 14 as a seed or propagule of the seed.

19. The transgenic plant material of claim 15 as a seed or propagule of the seed.

20. The transgenic plant material of claim 16 as a seed or propagule of the seed.

21. The transgenic plant material of claim 13, wherein the transgenic plant material is *Arabidopsis thaliana*, Carrot, sunflower, tobacco, tomato or potato.

22. The transgenic plant material of claim 14, wherein the transgenic plant material is *Arabidopsis thaliana*, carrot, sunflower, tobacco, tomato or potato.

23. The transgenic plant material of claim 15, wherein the transgenic plant material is *Arabidopsis thaliana*, carrot, sunflower, tobacco, tomato or potato.

24. The transgenic plant material of claim 16, wherein the transgenic plant material is *Arabidopsis thaliana*, carrot, sunflower, tobacco, tomato or potato.

25. The transgenic plant material of claim 17, wherein the transgenic plant material is *Arabidopsis thaliana*, carrot, sunflower, tobacco, tomato or potato.

26. The transgenic plant material of claim 18, wherein the transgenic plant material is *Arabidopsis thaliana*, carrot, sunflower, tobacco, tomato or potato.

27. The transgenic plant material of claim 19, wherein the transgenic plant material is *Arabidopsis thaliana*, carrot, sunflower, tobacco, tomato or potato.

28. The transgenic plant material of claim 20, wherein the transgenic plant material is *Arabidopsis thaliana*, carrot, sunflower, tobacco, tomato or potato.

29. A recombinant DNA construct capable of transforming plant material comprising a DNA sequence selected from the group consisting of:
   a) a first DNA sequence encoding an enzyme having catalytic activity of ketothiolase;
   b) a second DNA sequence encoding an enzyme having catalytic activity of acetoacetyl-CoA reductase; and
   c) a third DNA sequence encoding an enzyme having catalytic activity of polyhydroxyalkanoate synthase;
operably linked upstream (5') to a nucleic acid plant promoter and downstream (3') to a regulatory sequence containing a polyadenylation signal, such that upon transformation, the plant material produces the enzyme encoded by the selected DNA sequence.

30. The recombinant DNA construct of claim 29, wherein
   a) the first DNA sequence encodes an enzyme having the catalytic activity of an enzyme encoded by positions 2696–3877 of SEQ ID NO:1;
   b) the second DNA sequence encodes an enzyme having the catalytic activity of an enzyme encoded by positions 3952–4692 of SEQ ID NO:1; and
   c) the third DNA sequence encodes an enzyme having the catalytic activity of an enzyme encoded by positions 842–2611 of SEQ ID NO:1.

31. The recombinant DNA construct of claim 30, wherein
   a) the first DNA sequence encodes an enzyme encoded by positions 2696–3877 of SEQ ID NO:1;
   b) the second DNA sequence encodes an enzyme encoded by positions 3952–4692 of SEQ ID NO:1; and
   c) the third DNA sequence encodes an enzyme encoded by positions 842–2611 of SEQ ID NO:1.

32. The recombinant DNA construct of claim 31, wherein
   a) the first DNA sequence has the DNA sequence of positions 2696–3877 of SEQ ID NO:1;
   b) the second DNA sequence has the DNA sequence of positions 3952–4692 of SEQ ID NO:1; and
   c) the third DNA sequence has the DNA sequence of positions 842–2611 of SEQ ID NO:1.

33. A method for introducing foreign DNA into a plant wherein the foreign DNA encodes enzymes leading to the synthesis of a polyhydroxyalkanoate, the method comprising mating by sexual fertilization a first and a second plant which do not produce polyhydroxyalkanoate, wherein the first plant comprises a DNA sequence encoding an enzyme having catalytic activity of acetoacetyl-CoA reductase and the second plant comprises a DNA sequence encoding an enzyme having catalytic activity of polyhydroxyalkanoate synthase, such that progeny resulting from the sexual fertilization are capable of producing polyhydroxyalkanoate.

34. The method of claim 33, wherein the first plant further comprises a DNA sequence encoding an enzyme having catalytic activity of ketothiolase.

35. The method of claim 33, wherein the second plant further comprises a DNA sequence encoding an enzyme having catalytic activity of ketothiolase.

36. The method of claim 33, wherein the progeny produce one or more granules comprising polyhydroxybutyrate.

37. A transgenic plant material comprising:
   a) a first DNA sequence encoding an enzyme having catalytic activity of ketothiolase;
   b) a second DNA sequence encoding an enzyme having catalytic activity of acetoacetyl-CoA reductase; and
   c) a third DNA sequence encoding an enzyme having catalytic activity of polyhydroxyalkanoate synthase;
wherein at least the second DNA sequence and third DNA sequence are ectopic; and wherein expression of the DNA sequences leads to the production of polyhydroxyalkanoate in the plant material.

38. A method for producing polyhydroxyalkanoate comprising
   a) mating by sexual fertilization a first and a second plant which do not produce polyhydroxyalkanoate, wherein the first plant comprises a DNA sequence encoding an enzyme having catalytic activity of acetoacetyl-CoA reductase and the second plant comprises a DNA sequence encoding an enzyme having catalytic activity of polyhydroxyalkanoate synthase, such that progeny resulting from the sexual fertilization are capable of producing polyhydroxyalkanoate;
   b) recovering the polyhydroxyalkanoate from the progeny.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4983 Base Pairs
        ( B ) TYPE: Nucleic Acid
        ( C ) STRANDEDNESS: Double
        ( D ) TOPOLOGY: Linear ( i i ) MOLECULE TYPE:
        ( A ) DESCRIPTION: Genomic DNA ( i i i ) HYPOTHETICAL: No ( i v ) ANTI-SENSE: No ( v i ) ORIGINAL SOURCE:
        ( A ) ORGANISM: Alcaligenes eutrophus ( v i i ) IMMEDIATE SOURCE:
        ( A ) LIBRARY: Genomic ( x i ) SEQUENCE DESCRIPTION: SEQ ID NO: 1:

```
CCCGGGCAAG   TACCTTGCCG   ACATCTATGC   GCTGGCGCGC   ACGCGCCTGG       50

CGCGCGCCGG   CTGTACCGAG   GTCTACGGCG   GCGACGCCTG   CACCGTGGCC      100

GACGCCGGTC   GCTTCTACTC   CTATCGGCGC   GATGGCGTGA   CCGGCCGCAT      150

GGCCAGCCTG   GTCTGGCTGG   CGGACTGAGC   CCGCCGCTGC   CTCACTCGTC      200

CTTGCCCCTG   GCCGCCTGCG   CGCGCTCGGC   TTCAGCCTTG   CGTCGGCGGC      250
```

| | | | | | |
|---|---|---|---|---|---|
| GGCCGGGCGT | GCCCATGATG | TAGAGCACCA | CGCCACCGGC | GCCATGCCAT | 300 |
| ACATCAGGAA | GGTGGCAACG | CCTGCCACCA | CGTTGTGCTC | GGTGATCGCC | 350 |
| ATCATCAGCG | CCACGTAGAG | CCAGCCAATG | CCACGATGT | ACATCAAAAA | 400 |
| TTCATCCTTC | TCGCCTATGC | TCTGGGGCCT | CGGCAGATGC | GAGCGCTGCA | 450 |
| TACCGTCCGG | TAGGTCGGGA | AGCGTGCAGT | GCCGAGGCGG | ATTCCCGCAT | 500 |
| TGACAGCGCG | TGCGTTGCAA | GGCAACAATG | GACTCAAATG | TCTCGGAATC | 550 |
| GCTGACGATT | CCCAGGTTTC | TCCGGCAAGC | ATAGCGCATG | GCGTCTCCAT | 600 |
| GCGAGAATGT | CGCGCTTGCC | GGATAAAAGG | GGAGCCGCTA | TCGGAATGGA | 650 |
| CGCAAGCCAC | GGCCGCAGCA | GGTGCGGTCG | AGGGCTTCCA | GCCAGTTCCA | 700 |
| GGGCAGATGT | GCCGGCAGAC | CCTCCCGCTT | TGGGGAGGC | GCAAGCCGGG | 750 |
| TCCATTCGGA | TAGCATCTCC | CCATGCAAAG | TGCCGGCCAG | GGCAATGCCC | 800 |
| GGAGCCGGTT | CGAATAGTGA | CGGCAGAGAG | ACAATCAAAT | CATGATGGCG | 850 |

```
                                                               MetAla
                                                                  1
```

| | | | | | |
|---|---|---|---|---|---|
| ACCGGCAAAG | GCGCGGCAGC | TTCCACGCAG | GAAGGCAAGT | CCCAACCATT | 900 |
| ThrGlyLysG | lyAlaAlaAl | aSerThrGln | GluGlyLysS | erGlnProPh | |
| 5 | 10 | | 15 | | |
| CAAGGTCACG | CCGGGGCCAT | TCGATCCAGC | CACATGGCTG | GAATGGTCCC | 950 |
| eLysValThr | ProGlyProP | heAspProAl | aThrTrpLeu | GluTrpSerA | |
| 20 | 25 | 30 | | 35 | |
| GCCAGTGGCA | GGGCACTGAA | GGCAACGGCC | ACGCGGCCGC | GTCCGGCATT | 1000 |
| rgGlnTrpGl | nGlyThrGlu | GlyAsnGlyH | isAlaAlaAl | aSerGlyIle | |
| | 40 | 45 | | 50 | |
| CCGGGCCTGG | ATGCGCTGGC | AGGCGTCAAG | ATCGCGCCGG | CGCAGCTGGG | 1050 |
| ProGlyLeuA | spAlaLeuAl | aGlyValLys | IleAlaProA | laGlnLeuGl | |
| 55 | | 60 | | 65 | |
| TGATATCCAG | CAGCGCTACA | TGAAGGACTT | CTCAGCGCTG | TGGCAGGCCA | 1100 |
| yAspIleGln | GlnArgTyrM | etLysAspPh | eSerAlaLeu | TrpGlnAlaM | |
| 70 | 75 | | 80 | | 85 |
| TGGCCGAGGG | CAAGGCCGAG | GCCACCGGTC | CGCTGCACGA | CCGGCGCTTC | 1150 |
| etAlaGluGl | yLysAlaGlu | AlaThrGlyP | roLeuHisAs | pArgArgPhe | |
| | 90 | 95 | | 100 | |
| GCCGGCGACG | CATGGCGCAC | CAACCTCCCA | TATCGCTTCG | CTGCCGCGTT | 1200 |
| AlaGlyAspA | laTrpArgTh | rAsnLeuPro | TyrArgPheA | laAlaAlaPh | |
| 105 | | 110 | | 115 | |
| CTACCTGCTC | AATGCGCGCG | CCTTGACCGA | GCTGGCCGAT | GCCGTCGAGG | 1250 |
| eTyrLeuLeu | AsnAlaArgA | laLeuThrGl | uLeuAlaAsp | AlaValGluA | |
| 120 | 125 | | 130 | | 135 |
| CCGATGCCAA | GACCCGCCAG | CGCATCCGCT | TCGCGATCTC | GCAATGGGTC | 1300 |
| laAspAlaLy | sThrArgGln | ArgIleArgP | heAlaIleSe | rGlnTrpVal | |
| | 140 | 145 | | 150 | |
| GATGCGATGT | CGCCCGCCAA | CTTCCTTGCC | ACCAATCCCG | AGGCGCAGCG | 1350 |
| AspAlaMetS | erProAlaAs | nPheLeuAla | ThrAsnProG | luAlaGlnAr | |
| 155 | | 160 | | 165 | |
| CCTGCTGATC | GAGTCGGGCG | GCGAATCGCT | GCGTGCCGGC | GTGCGCAACA | 1400 |
| gLeuLeuIle | GluSerGlyG | lyGluSerLe | uArgAlaGly | ValArgAsnM | |
| 170 | | 175 | | 180 | 185 |
| TGATGGAAGA | CCTGACACGC | GGCAAGATCT | CGCAGACCGA | CGAGAGCGCG | 1450 |
| etMetGluAs | pLeuThrArg | GlyLysIleS | erGlnThrAs | pGluSerAla | |
| | 190 | | 195 | | 200 |
| TTTGAGGTCG | GCCGCAATGT | CGCGGTGACC | GAAGGCGCCG | TGGTCTTCGA | 1500 |
| PheGluValG | lyArgAsnVa | lAlaValThr | GluGlyAlaV | alValPheGl | |
| 205 | | 210 | | 215 | |

| | | | | | |
|---|---|---|---|---|---|
| GAACGAGTAC | TTCCAGCTGT | TGCAGTACAA | GCCGCTGACC | GACAAGGTGC | 1550 |
| uAsnGluTyr 220 | PheGlnLeuL 225 | euGlnTyrLy | sProLeuThr 230 | AspLysValH 235 | |
| ACGCGCGCCC | GCTGCTGATG | GTGCCGCCGT | GCATCAACAA | GTACTACATC | 1600 |
| isAlaArgPr | oLeuLeuMet 240 | ValProProC 245 | ysIleAsnLy | sTyrTyrIle 250 | |
| CTGGACCTGC | AGCCGGAGAG | CTCGCTGGTG | CGCCATGTGG | TGGAGCAGGG | 1650 |
| LeuAspLeuG 255 | lnProGluSe | rSerLeuVal 260 | ArgHisValV 265 | alGluGlnGl | |
| ACATACGGTG | TTTCTGGTGT | CGTGGCGCAA | TCCGGACGCC | AGCATGGCCG | 1700 |
| yHisThrVal 270 | PheLeuValS 275 | erTrpArgAs 280 | nProAspAla | SerMetAlaG 285 | |
| GCAGCACCTG | GGACGACTAC | ATCGAGCACG | CGGCCATCCG | CGCCATCGAA | 1750 |
| lySerThrTr 290 | pAspAspTyr | IleGluHisA 295 | laAlaIleAr 300 | gAlaIleGlu | |
| GTCGCGCGCG | ACATCAGCGG | CCAGGACAAG | ATCAACGTGC | TCGGCTTCTG | 1800 |
| ValAlaArgA 305 | spIleSerGl 310 | yGlnAspLys | IleAsnValL 315 | euGlyPheCy | |
| CGTGGGCGGC | ACCATTGTCT | CGACCGCGCT | GGCGGTGCTG | GCCGCGCGCG | 1850 |
| sValGlyGly 320 | ThrIleValS 325 | erThrAlaLe | uAlaValLeu 330 | AlaAlaArgG 335 | |
| GCGAGCACCC | GGCCGCCAGC | GTCACGCTGC | TGACCACGCT | GCTGGACTTT | 1900 |
| lyGluHisPr 340 | oAlaAlaSer | ValThrLeuL 345 | euThrThrLe 350 | uLeuAspPhe | |
| GCCGACACGG | GCATCCTCGA | CGTCTTTGTC | GACGAGGGCC | ATGTGCAGTT | 1950 |
| AlaAspThrG 355 | lyIleLeuAs 360 | pValPheVal | AspGluGlyH 365 | isValGlnLe | |
| GCGCGAGGCC | ACGCTGGGCG | GCGGCGCCGG | CGCCGTGC | GCGCTGCTGC | 2000 |
| uArgGluAla 370 | ThrLeuGlyG 375 | lyGlyAlaGl | yAlaProCys 380 | AlaLeuLeuA 385 | |
| GCGGCCTTGA | GCTGGCCAAT | ACCTTCTCGT | TCTTGCGCCC | GAACGACCTG | 2050 |
| rgGlyLeuGl | uLeuAlaAsn 390 | ThrPheSerP 395 | heLeuArgPr | oAsnAspLeu 400 | |
| GTGTGGAACT | ACGTGGTCGA | CAACTACCTG | AAGGGCAACA | CGCCGGTGCC | 2100 |
| ValTrpAsnT 405 | yrValValAs | pAsnTyrLeu 410 | LysGlyAsnT 415 | hrProValPr | |
| GTTCGACCTG | CTGTTCTGGA | ACGGCGACGC | CACCAACCTG | CCGGGGCCGT | 2150 |
| oPheAspLeu 420 | LeuPheTrpA 425 | snGlyAspAl | aThrAsnLeu 500 | ProGlyProT 505 | |
| GGTACTGCTG | GTACCTGCGC | CACACCTACC | TGCAGAACGA | GCTCAAGGTA | 2200 |
| rpTyrCysTr | pTyrLeuArg 510 | HisThrTyrL 515 | euGlnAsnGl | uLeuLysVal 520 | |
| CCGGGCAAGC | TGACCGTGTG | CGGCGTGCCG | GTGGACCTGG | CCAGCATCGA | 2250 |
| ProGlyLysL 525 | euThrValCy | sGlyValPro 530 | ValAspLeuA 535 | laSerIleAs | |
| CGTGCCGACC | TATATCTACG | GCTCGCGCGA | AGACCATATC | GTGCCGTGGA | 2300 |
| pValProThr 540 | TyrIleTyrG 545 | lySerArgGl | uAspHisIle 550 | ValProTrpT 555 | |
| CCGCGGCCTA | TGCCTCGACC | GCGCTGCTGG | CGAACAAGCT | GCGCTTCGTG | 2350 |
| hrAlaAlaTy | rAlaSerThr 560 | AlaLeuLeuA 565 | laAsnLysLe | uArgPheVal 570 | |
| CTGGGTGCGT | CGGGCCATAT | CGCCGGTGTG | ATCAACCCGC | CGGCCAAGAA | 2400 |
| LeuGlyAlaS 575 | erGlyHisIl | eAlaGlyVal 580 | IleAsnProP 585 | roAlaLysAs | |
| CAAGCGCAGC | CACTGGACTA | ACGATGCGCT | GCCGGAGTCG | CCGCAGCAAT | 2450 |
| nLysArgSer 590 | HisTrpThrA 595 | snAspAlaLe | uProGluSer 600 | ProGlnGlnT 605 | |
| GGCTGGCCGG | CGCCATCGAG | CATCACGGCA | GCTGGTGGCC | GGACTGGACC | 2500 |
| rpLeuAlaGl | yAlaIleGlu 610 | HisHisGlyS 615 | erTrpTrpPr | oAspTrpThr 620 | |

| | | | | | |
|---|---|---|---|---|---|
| GCATGGCTGG | CCGGGCAGGC | CGGCGCGAAA | CGCGCCGCGC | CCGCCAACTA | 2550 |
| AlaTrpLeuA | laGlyGlnAl | aGlyAlaLys | ArgAlaAlaP | roAlaAsnTy | |
| 625 | | 630 | 635 | | |
| TGGCAATGCG | CGCTATCGCG | CAATCGAACC | CGCGCCTGGG | CGATACGTCA | 2600 |
| rGlyAsnAla | ArgTyrArgA | laIleGluPr | oAlaProGly | ArgTyrValL | |
| 640 | 645 | | 650 | 655 | |
| AAGCCAAGGC | ATGACGCTTG | CATGAGTGCC | GGCGTGCGTC | ATGCACGGCG | 2650 |
| ysAlaLysAl | a | | | | |
| CCGGCAGGCC | TGCAGGTTCC | CTCCCGTTTC | CATTGAAAGG | ACTACACAAT | 2700 |
| | | | | Me | |
| | | | | 1 | |
| GACTGACGTT | GTCATCGTAT | CCGCCGCCCG | CACCGCGGTC | GGCAAGTTTG | 2750 |
| tThrAspVal | ValIleValS | erAlaAlaAr | gThrAlaVal | GlyLysPheG | |
| | 5 | | 10 | 15 | |
| GCGGCTCGCT | GGCCAAGATC | CCGGCACCGG | AACTGGGTGC | CGTGGTCATC | 2800 |
| lyGlySerLe | uAlaLysIle | ProAlaProG | luLeuGlyAl | aValValIle | |
| 20 | | 25 | 30 | | |
| AAGGCCGCGC | TGGAGCGCGC | CGGCGTCAAG | CCGGAGCAGG | TGAGCGAAGT | 2850 |
| LysAlaAlaL | euGluArgAl | aGlyValLys | ProGluGlnV | alSerGluVa | |
| 35 | 40 | | 45 | 50 | |
| CATCATGGGC | CAGGTGCTGA | CCGCCGGTTC | GGGCCAGAAC | CCCGCACGCC | 2900 |
| lIleMetGly | GlnValLeuT | hrAlaGlySe | rGlyGlnAsn | ProAlaArgG | |
| | 55 | 60 | | 65 | |
| AGGCCGCGAT | CAAGGCCGGC | CTCGGCGCGA | TGGTGCCGGC | CATGACCATC | 2950 |
| lnAlaAlaIl | eLysAlaGly | LeuGlyAlaM | etValProAl | aMetThrIle | |
| 70 | | 75 | 80 | | |
| AACAAGGTGT | GCGGCTCGGG | CCTGAAGGCC | GTGATGCTGG | CCGCCAACGC | 3000 |
| AsnLysValC | ysGlySerGl | yLeuLysAla | ValMetLeuA | laAlaAsnAl | |
| 85 | 90 | | 95 | 100 | |
| GATCATGGCG | GGCGACGCCG | AGATCGTGGT | GGCCGGCGGC | CAGGAAAACA | 3050 |
| aIleMetAla | GlyAspAlaG | luIleValVa | lAlaGlyGly | GlnGluAsnM | |
| | 105 | 110 | | 115 | |
| TGAGCGCCGC | CCCGCACGTG | CTGCCGGGCT | CGCGCGATGG | TTTCCGCATG | 3100 |
| etSerAlaAl | aProHisVal | LeuProGlyS | erArgAspGl | yPheArgMet | |
| 120 | | 125 | 130 | | |
| GGCGATGCCA | AGCTGGTCGA | CACCATGATC | GTCGACGGCC | TGTGGGACGT | 3150 |
| GlyAspAlaL | ysLeuValAs | pThrMetIle | ValAspGlyL | euTrpAspVa | |
| 135 | 140 | | 145 | 150 | |
| GTACAACCAG | TACCACATGG | GCATCACCGC | CGAGAACGTG | GCCAAGGAAT | 3200 |
| lTyrAsnGln | TyrHisMetG | lyIleThrAl | aGluAsnVal | AlaLysGluT | |
| | 155 | 160 | | 165 | |
| ACGGCATCAC | ACGCGAGGCG | CAGGATGAGT | TCGCCGTCGG | CTCGCAGAAC | 3250 |
| yrGlyIleTh | rArgGluAla | GlnAspGluP | heAlaValGl | ySerGlnAsn | |
| 170 | | 175 | 180 | | |
| AAGGCCGAAG | CCGCGCAGAA | GGCCGGCAAG | TTTGACGAAG | AGATCGTCCC | 3300 |
| LysAlaGluA | laAlaGlnLy | sAlaGlyLys | PheAspGluG | luIleValPr | |
| 185 | 190 | | 195 | 200 | |
| GGTGCTGATC | CCGCAGCGCA | AGGGCGACCC | GGTGGCCTTC | AAGACCGACG | 3350 |
| oValLeuIle | ProGlnArgL | ysGlyAspPr | oValAlaPhe | LysThrAspG | |
| | 205 | 210 | | 215 | |
| AGTTCGTGCG | CCAGGGCGCC | ACGCTGGACA | GCATGTCCGG | CCTCAAGCCC | 3400 |
| luPheValAr | gGlnGlyAla | ThrLeuAspS | erMetSerGl | yLeuLysPro | |
| 220 | | 225 | 230 | | |
| GCCTTCGACA | AGGCCGGCAC | GGTGACCGCG | GCCAACGCCT | CGGGCCTGAA | 3450 |
| AlaPheAspL | ysAlaGlyTh | rValThrAla | AlaAsnAlaS | erGlyLeuAs | |
| 235 | 240 | | 245 | 250 | |
| CGACGGCGCC | GCCGCGGTGG | TGGTGATGTC | GGCGGCCAAG | GCCAAGGAAC | 3500 |
| nAspGlyAla | AlaAlaValV | alValMetSe | rAlaAlaLys | AlaLysGluL | |
| | 255 | 260 | | 265 | |

| | | | | | |
|---|---|---|---|---|---|
| TGGGCCTGAC | CCCGCTGGCC | ACGATCAAGA | GCTATGCCAA | CGCCGGTGTC | 3550 |
| euGlyLeuTh 270 | rProLeuAla | ThrIleLysS 275 | erTyrAlaAs 280 | nAlaGlyVal | |
| GATCCCAAGG | TGATGGGCAT | GGGCCCGGTG | CCGGCCTCCA | AGCGCGCCCT | 3600 |
| AspProLysV 285 | alMetGlyMe 290 | tGlyProVal | ProAlaSerL 295 | ysArgAlaLe 300 | |
| GTCGCGCGCC | GAGTGGACCC | CGCAAGACCT | GGACCTGATG | GAGATCAACG | 3650 |
| uSerArgAla | GluTrpThrP 305 | roGlnAspLe 310 | uAspLeuMet | GluIleAsnG 315 | |
| AGGCCTTTGC | CGCGCAGGCG | CTGGCGGTGC | ACCAGCAGAT | GGGCTGGGAC | 3700 |
| luAlaPheAl 320 | aAlaGlnAla | LeuAlaValH 325 | isGlnGlnMe 330 | tGlyTrpAsp | |
| ACCTCCAAGG | TCAATGTGAA | CGGCGGCGCC | ATCGCCATCG | GCCACCCGAT | 3750 |
| ThrSerLysV 335 | alAsnValAs 340 | nGlyGlyAla | IleAlaIleG 345 | lyHisProIl 350 | |
| CGGCGCGTCG | GGCTGCCGTA | TCCTGGTGAC | GCTGCTGCAC | GAGATGAAGC | 3800 |
| eGlyAlaSer | GlyCysArgI 355 | leLeuValTh 360 | rLeuLeuHis | GluMetLysA 365 | |
| GCCGTGACGC | GAAGAAGGGC | CTGGCCTCGC | TGTGCATCGG | CGGCGGCATG | 3850 |
| rgArgAspAl 370 | aLysLysGly | LeuAlaSerL 375 | euCysIleGl 380 | yGlyGlyMet | |
| GGCGTGGCGC | TGGCAGTCGA | GCGCAAATAA | GGAAGGGGTT | TTCCGGGGCC | 3900 |
| GlyValAlaL 385 | euAlaValGl 390 | uArgLys | | | |
| GCGCGCGGTT | GGCGCGGACC | CGGCGACGAT | AACGAAGCCA | ATCAAGGAGT | 3950 |
| GGACATGACT | CAGCGCATTG | CGTATGTGAC | CGGCGGCATG | GGTGGTATCG | 4000 |
| MetThr 1 | GlnArgIleA 5 | laTyrValTh 10 | rGlyGlyMet | GlyGlyIleG 15 | |
| GAACCGCCAT | TTGCCAGCGG | CTGGCCAAGG | ATGGCTTTCG | TGTGGTGGCC | 4050 |
| lyThrAlaIl | eCysGlnArg 20 | LeuAlaLysA 25 | spGlyPheAr | gValValAla 30 | |
| GGTTGCGGCC | CCAACTCGCC | GCGCCGCGAA | AAGTGGCTGG | AGCAGCAGAA | 4100 |
| GlyCysGlyP 35 | roAsnSerPr 40 | oArgArgGlu | LysTrpLeuG 45 | luGlnGlnLy | |
| GGCCCTGGGC | TTCGATTTCA | TTGCCTCGGA | AGGCAATGTG | GCTGACTGGG | 4150 |
| sAlaLeuGly 50 | PheAspPheI 55 | leAlaSerGl | uGlyAsnVal 60 | AlaAspTrpA 65 | |
| ACTCGACCAA | GACCGCATTC | GACAAGGTCA | AGTCCGAGGT | CGGCGAGGTT | 4200 |
| spSerThrLy | sThrAlaPhe 70 | AspLysValL 75 | ysSerGluVa | lGlyGluVal 80 | |
| GATGTGCTGA | TCAACAACGC | CGGTATCACC | CGCGACGTGG | TGTTCCGCAA | 4250 |
| AspValLeuI 85 | leAsnAsnAl | aGlyIleThr 90 | ArgAspValV 95 | alPheArgLy | |
| GATGACCCGC | GCCGACTGGG | ATGCGGTGAT | CGACACCAAC | CTGACCTCGC | 4300 |
| sMetThrArg 100 | AlaAspTrpA 105 | spAlaValIl | eAspThrAsn 110 | LeuThrSerL 115 | |
| TGTTCAACGT | CACCAAGCAG | GTGATCGACG | GCATGGCCGA | CCGTGGCTGG | 4350 |
| euPheAsnVa | lThrLysGln 120 | ValIleAspG 125 | lyMetAlaAs | pArgGlyTrp 130 | |
| GGCCGCATCG | TCAACATCTC | GTCGGTGAAC | GGGCAGAAGG | GCCAGTTCGG | 4400 |
| GlyArgIleV 135 | alAsnIleSe 140 | rSerValAsn | GlyGlnLysG 145 | lyGlnPheGl | |
| CCAGACCAAC | TACTCCACCG | CCAAGGCCGG | CCTGCATGGC | TTCACCATGG | 4450 |
| yGlnThrAsn 150 | TyrSerThrA 155 | laLysAlaGl | yLeuHisGly 160 | PheThrMetA 165 | |
| CACTGGCGCA | GGAAGTGGCG | ACCAAGGGCG | TGACCGTCAA | CACGGTCTCT | 4500 |
| laLeuAlaGl 170 | nGluValAla 175 | ThrLysGlyV | alThrValAs 180 | nThrValSer | |
| CCGGGCTATA | TCGCCACCGA | CATGGTCAAG | GCGATCCGCC | AGGACGTGCT | 4550 |
| ProGlyTyrI | leAlaThrAs | pMetValLys | AlaIleArgG | lnAspValLe | |

```
              185                 190                 195

CGACAAGATC  GTCGCGACGA  TCCCGGTCAA  GCGCCTGGGC  CTGCCGGAAG        4600
        uAspLysIle  ValAlaThrI  leProValLy  sArgLeuGly  LeuProGluG
        200                     205                     210                     215

AGATCGCCTC  GATCTGCGCC  TGGTTGTCGT  CGGAGGAGTC  CGGTTTCTCG        4650
        luIleAlaSe  rIleCysAla  TrpLeuSerS  erGluGluSe  rGlyPheSer
                    220                     225                     230

ACCGGCGCCG  ACTTCTCGCT  CAACGGCGGC  CTGCATATGG  GCTGACCTGC        4700
        ThrGlyAlaA  spPheSerLe  uAsnGlyGly  LeuHisMetG  ly
        235                     240                     245

CGGCCTGGTT  CAACCAGTCG  GCAGCCGGCG  CTGGCGCCCG  CGTATTGCGG        4750

TGCAGCCAGC  GCGGCGCACA  AGGCGGCGGG  CGTTTCGTTT  CGCCGCCCGT        4800

TTCGCGGCAA  GGCCCGCGAA  TCGTTTCTGC  CCGCGCGGCN  TTCCTCGCTT        4850

TTTGCGCCAA  TTCACCGGGT  TTTCCTTTAA  GCCCCGTCGC  TTTTCTTAGT        4900

GCCTTGTTGG  GCATAGAATC  AGGGCAGCGG  CGCAGCCAGC  ACCATGTTCG        4950

TGCAGCGCGG  CCCTCGCGGG  GGCGAGGCTG  CAG                           4983
```